US011752168B2

(12) United States Patent
Loing et al.

(10) Patent No.: US 11,752,168 B2
(45) Date of Patent: Sep. 12, 2023

(54) METHODS OF USING COSMETIC COMPOSITIONS COMPRISING EXOPOLYSACCHARIDES DERIVED FROM MICROBIAL MATS

(71) Applicant: Lucas Meyer Cosmetics Canada Inc., Québec (CA)

(72) Inventors: Estelle Loing, Québec (CA); Sandrine Briatte, Saint-Rédempteur (CA); Patrice Dionne, Saint-Rédempteur (CA); Martin Beaulieu, Rimouski (CA); Xavier Moppert, Punaauia (PF); Laurent Richert, Pirac (PF); Catherine Vayssier, Québec (CA)

(73) Assignee: LUCAS MEYER COSMETICS CANADA INC., Quebec (CA)

( * ) Notice: Subject to any disclaimer, the term of this patent is extended or adjusted under 35 U.S.C. 154(b) by 220 days.

(21) Appl. No.: 17/302,784

(22) Filed: May 12, 2021

(65) Prior Publication Data

US 2021/0330691 A1 Oct. 28, 2021

Related U.S. Application Data

(60) Division of application No. 15/979,011, filed on May 14, 2018, now Pat. No. 11,040,058, which is a continuation of application No. 12/988,211, filed as application No. PCT/CA2009/000493 on Apr. 15, 2009, now abandoned.

(60) Provisional application No. 61/044,992, filed on Apr. 15, 2008.

(51) Int. Cl.
| | | |
|---|---|---|
| *A61K 31/715* | (2006.01) | |
| *A61K 8/73* | (2006.01) | |
| *A61K 8/99* | (2017.01) | |
| *A61Q 19/08* | (2006.01) | |

(52) U.S. Cl.
CPC .............. *A61K 31/715* (2013.01); *A61K 8/73* (2013.01); *A61K 8/99* (2013.01); *A61Q 19/08* (2013.01)

(58) Field of Classification Search
CPC .......... A61K 31/715; A61K 8/73; A61K 8/99; A61K 2800/74; A61Q 19/08; A61Q 19/00; A61P 17/00; C12R 2001/445; C12R 2001/45; C12N 1/205
See application file for complete search history.

(56) References Cited

U.S. PATENT DOCUMENTS

| | | | |
|---|---|---|---|
| 5,965,127 | A | 10/1999 | Lemoine |
| 6,147,054 | A | 11/2000 | De Paoli |
| 6,344,346 | B1 | 2/2002 | Alami |
| 2002/0187167 | A1 | 12/2002 | Vacher |
| 2005/0265944 | A1 | 12/2005 | Cowden |
| 2006/0057131 | A1 | 3/2006 | Simard |
| 2007/0009455 | A1 | 2/2007 | Kim |
| 2007/0166266 | A1 | 7/2007 | Dillon |
| 2007/0259833 | A1 | 11/2007 | Matou |
| 2008/0131472 | A1 | 6/2008 | Senni |
| 2009/0238782 | A1 | 9/2009 | Vacher |
| 2011/0150795 | A1 | 6/2011 | Loing |
| 2011/0245199 | A1 | 10/2011 | Senni |
| 2018/0256627 | A1 | 9/2018 | Loing |

FOREIGN PATENT DOCUMENTS

| | | |
|---|---|---|
| CA | 2155134 A1 | 2/1996 |
| CA | 2235177 C | 1/1999 |
| CA | 2279064 A1 | 1/2000 |
| CN | 101904804 A | 12/2010 |
| EP | 0699689 A1 | 3/1996 |
| EP | 0889135 A1 | 1/1999 |
| EP | 0987010 B1 | 3/2000 |
| FR | 2781673 A1 | 2/2004 |
| JP | 08-277303 A | 10/1996 |
| JP | 11-49801 A | 2/1999 |
| JP | 2001-516375 A | 9/2001 |
| JP | 2005015375 A | 1/2005 |
| JP | 2005-513076 A | 5/2005 |
| JP | 2005-527498 A | 9/2005 |
| JP | 2008-502762 A | 1/2008 |
| JP | 2008-502763 A | 1/2008 |
| WO | 9318174 A1 | 9/1993 |
| WO | 98/35993 A1 | 8/1998 |
| WO | 199835993 A1 | 8/1998 |
| WO | 03053158 A1 | 7/2003 |
| WO | 200368243 A1 | 8/2003 |

(Continued)

OTHER PUBLICATIONS

Gautret, P., et al., Automicrites in modern cyanobacterial stromatolitic deposits of Rangiroa, Tuamotu Archipelago, French Polynesia: Biochemical parameters underiaying their formation, Sedimentary Geology, 2005, 178:55-73.

(Continued)

*Primary Examiner* — Renee Claytor
*Assistant Examiner* — Susan E. Fernandez
(74) *Attorney, Agent, or Firm* — Lavery, de Billy, L.L.P.; Julie Gauvreau

(57) ABSTRACT

A skin care composition is disclosed comprising at least one exopolysaccharide (EPS) originating from a microbial mat, the EPS being in a concentration of about 0.001% w/w to about 1.5% w/w of the composition. Uses and methods of use thereof. In specific embodiments, the EPSs are derived from microorganisms isolated from microbial mats found in French Polynesia. The composition is useful in reducing signs of skin aging and environmental damage by altering skin cell metabolism and improving hydration.

14 Claims, 16 Drawing Sheets

(56) References Cited

FOREIGN PATENT DOCUMENTS

| | | |
|---|---|---|
| WO | 2006/003290 A2 | 1/2006 |
| WO | 200603290 A2 | 1/2006 |
| WO | 2010067327 A1 | 6/2010 |

OTHER PUBLICATIONS

Guezennec, J., et al., Microbial mats in French Polynesia and their biological applications, Process Biochemistry, 2011, 46(1):16-22.
Kim, S.K., et al., Prospective of the cosmeceuticals derived from marine organisms, Biotechnology and Bioprocess Engineering, 2008, 13:511-523.
Kligman, L.H., et al., Biochemical changes in hairless mouse skin collagen after chronic exposure to UVA radiation, Photoderm. Photobiol., 1991, 54(2): 233-237.
Mao Che, L., et al., Physical, chemical, and microbiological characteristics of microbial mats (KOPARA) in the South Pacific atolls of French Polynesia, Can. J. Microbiol., 2001, 47: 994-1012.
Raguenes, G., et al., A novel exopolymer-producing bacterium, *Paracoccus zeaxanthinifaciens* subsp. payriae, isolated from a "kopara" mat located in Rangiroa, an atoll of French Polynesia, Current Microbiology, 2004, 49:145-151.
Remington, The Science and Practice of Pharmacy, 19th Ed., Easton, Pa.: Mack Publishing Co., 1995, p. 1399-1404.
Richert, L., et al., Cyanobacterial populations that build 'kopara' microbial mats in Rangiroa, Tuamotu Archipelago, French Polynesia, European Journal of Phycology, 2006, 41(3): 259-279.
Richert, L., et al., Characterization of Exopolysaccharides Produced by Cyanobacteria Isolated from Polynesian Microbial Mats, Current Microbiology, 2005, 51: 379-384.
Rougeaux, H., et al., Microbial communities and exopolysaccharides from Polynesian mats, Mar. Biotechnol., 2001, 3:181-187.
International Search Report and Written Opinion dated Jul. 13, 2009 in PCT/CA2009/000493.
International Preliminary Report on Patentability dated Oct. 28, 2010 in PCT/CA2009/000493.
English translation of Office Action dated Nov. 9, 2011 in Chinese patent application No. 200980122383.7.
Ma Y et al. Vertical distribution and phylogenetic composition of bacteria in the Eastern Tropical North Pacific Ocean. Microbiological Research. 2009. 164: 624-633. Published Apr. 2, 2008 (Year: 2008).
Poli, Annarita, et al., "Bacterial Exopolysaccharides from Extreme Marine Habitats: Production, Characterization and Biological Activities", Mar. Drugs 2010, 8, 1779-1802; doi:10.3390/md8061779, (Jun. 3, 2010), 1779-1802.
JP 2005015375 Machine Translation. 2005. (Year: 2005).
CN 101904804 Machine Translation. 2010. (Year: 2010).
Drouillard, Set al. Structure of an amino acid-decorated exopolysaccharide secreted by a Vibrio alginolyticus strain. Marine Drugs. 2015.13: 6723-6739. Published Oct. 30, 2015. (Year: 2015).
Canadian Application Serial No. 2,720,542, Office Action dated Feb. 9, 2015, 4 pgs.
Chinese Application Serial No. 200980122383.7, Office Action dated Apr. 25, 2013, (English Translation), 4 pgs.
Chinese Application Serial No. 200980122383.7, Office Action dated Oct. 31, 2012, (English Translation), 5 pgs.
Chinese Application Serial No. 200980122383.7, Office Action dated Nov. 9, 2011, (English Translation), 6 pgs.
European Application No. 09732860.3, Office Action dated Apr. 13, 2015, 1 pg.
European Application No. 09732860.3, Office Action dated Jul. 16, 2015, 4 pgs.
European Application No. 09732860.3, Reply filed Jul. 10, 2015 to Office Action dated Apr. 13, 2015, 31 pgs.
European Application No. 09732860.3, Reply filed Jul. 20, 2015 to Office Action dated Jul. 16, 2015, 10 pgs.
Japanese Application Serial No. 2011-504293, Office Action dated Dec. 22, 2014, (English Translation), 2 pgs.
Korean Application Serial No. 10-2010-7024825, Office Action dated Oct. 21, 2014, (English Translation), 5 pgs.
Mexican Application Serial No. 10/11334, Office Action dated Jan. 8, 2015, (English Translation), 2 pgs.
Mexican Application Serial No. 10/11334, Office Action dated Jun. 15, 2014, (English Translation), 2 pgs.
Unipex product brochure, (2008), 1-12.
U.S. Appl. No. 12/988,211 Amendment & Response under 37 C. F. R. 1.114 dated Apr. 5, 2017, 11 oas.
U.S. Appl. No. 12/988,211, Advisory Action dated Nov. 23, 2016, 3 pgs.
U.S. Appl. No. 12/988,211, Final Office Action dated Aug. 8, 2016, 12 pgs.
U.S. Appl. No. 12/988,211, Final Office Action dated Nov. 15, 2017, 8pgs.
U.S. Appl. No. 12/988,211, Final Office Action dated Nov. 19, 2014, 17 pgs.
U.S. Appl. No. 12/988,211, Non Final Office Action dated Feb. 19, 2014, 23 pgs.
U.S. Appl. No. 12/988,211, Non Final Office Action dated Nov. 3, 2015, 11 oas.
U.S. Appl. No. 12/988,211, Non-Final Office Action dated Apr. 5, 2017, 9 pgs.
U.S. Appl. No. 12/988,211, Preliminary Amendment filed Nov. 15, 2010, 7 pgs.
U.S. Appl. No. 12/988,211, Response filed Jan. 14, 2014 to Restriction Requirement dated Nov. 10, 2013, 10 pgs.
U.S. Appl. No. 12/988,211, Response filed Feb. 6, 2017 to Advisory Action dated Nov. 23, 2016, 15 pqs.
U.S. Appl. No. 12/988,211, Response filed May 3, 2016 to Non Final Office Action dated Nov. 3, 2015, 16 pga.
U.S. Appl. No. 12/988,211, Response filed May 15, 2014 to Non Final Office Action dated Feb. 19, 2014, 35 pgs.
U.S. Appl. No. 12/988,211, Response filed May 19, 2015 to Final Office Action dated Nov. 19, 2014, 19 pgs.
U.S. Appl. No. 12/988,211, Response filed Nov. 8, 2016 to Final Office Action dated Aug. 8, 2016, 15 pgs.
U.S. Appl. No. 12/988,211, Restriction Requirement dated Nov. 20, 2013, 9 pgs.
Brazil Application No. PI0910937-4, Technical Examination Report dated Mar. 16, 2017, dated Mar. 16, 2017), 11 pgs.
European Application No. 09732860.3, Communication Pursuant to Article 94(3) EPC dated Aug. 24, 2016, (dated Aug. 24, 2016), 8 pgs.
European Application No. 09732860.3, Extended Search Report dated Mar. 23, 2015, 8 pgs.
Japanese Application Serial No. 2011-504293, Office Action dated Nov. 26, 2013, (w/ English Translation), 13 pgs.
"Mexican Application No. 10/11334, English Translation of Official Communication dated Mar. 7, 2016", (dated Mar. 7, 2016), 6 DOS.
"Polyglucuronic acids, stractures, function and degrading enzymes", Carbohydrate IPolymers, vol. 84, (2011), 1-13.
"Remington: The Science and Practice of Pharmacy", 19th Edition, Easton, PA, Mack Publishina Co., (1995), 1399-1404.
"Technical file for Exossine TM, purified exopolysaccharrides synthesized by Kopara microorQanism", Lucasmeyer cosmetic, publication 1, 1-27 No Date.
UNIPEX Innovations, publication 3, Exossine TM, Exo-H TM, Exo-T TM, Exo-P TM, 6 pg•s.
Barbier, Georges, et al., "*Vibrio diabolicus* sp_ Nov_, a New Polysaccharide-Secreting Organism Isolated from a Deep-sea Hydrothermal Vent Polychaete Annelid", Alvinella Ipompejana, Int. J. Systematic BacterioloQy, (1997), 989-995.
Boisset, C, et al., "Structural data on a bacterial exopolysaccharide produced by a deep-sea Alteromonas macleodii strain", Carbohydrate polymers, 2012 vol. 90, 49-59.
Cambon-Bonavita, M. A., et al., "A novel polymer produced by a bacterium isolated from a deep-sea hydrothermal vent polychaete annelid", Journal of Applied Microbiology, vol. 93 '2) (2002) 310-315, (Aug. 1, 2002), 310.
Estelle, Loing, "Who is Lucas Meyer Cosmetics", PPT presentation, slide 2, (2013), 1-15.

(56) References Cited

OTHER PUBLICATIONS

Guezennec, J, et al., "A novel polymer produced by a bacterium isolated from a deep-sea hydrothermal vent polychaete annelid", Journal of Aoolied Microbiology 2002, 93, 310-315.

Guezennec, J. G., et al., "Preliminary chemical characterization of unusual eubacterial exopolysaccharides of deep-sea origin", Carbohydrate Polymers, vol. 25 (4) (1994) 287-294, 'Jan. 1, 1994), 287-294.

Kligman, L. H, et al., "The Contributions of UVA and UVB to Connective Tissue Damage in Hairless Mice", Journal of Investiaative Dermatoloav, 84(4), (1985), 272-276.

Lopez-Lopez, A., et al., "Genetic analysis of housekeeping genes reveals a deep-sea ecotype of Alteromonas macleodii in the Mediterranean Sea", Environmental Microbiology, 7(5), Summary, (2005), 1 Pa.

Mao Che, L., et al., "Physical, chemical, and microbiological characteristics of microbial mats (KOPARA) in the South Pacific atolls of French Polynesia", Canadian Journal of Microbioloav, 47(11), (Nov. 2001), 994-1012.

Paerl, et al., "Ubiquity of heterotropic diazotropic in marine microbial mats", Aquat Micro. Ecol., vol. 19, (1999), 29-36.

Rougeaux, H., et al., "Novel bacterial exopolysaccharides from deep-sea hydrothermal vents", Carbohvdrate Polvmers 31 /4) /1996) 237-242, /Dec. 1, 1996), 237-242.

Sutherland, "Novel and established application of microbial polysaccharides", Tibtech, vol. 16, (1998), 41-46.

Tavernia, "beta-(1,4)-polyglucuronic acids—an overview", The Open Biotechnology Journal, vol. 2, /2008), 73-86.

U.S. Appl. No. 15/979,011, Restriction requirement dated Nov. 20, 2019, 5 pgs.

U.S. Appl. No. 15/979,011, Non Final Office Action, dated Apr. 30, 2020, 16 pgs.

U.S. Appl. No. 15/979,011, Final Office Action, dated Jan. 4, 2021, 13 pgs.

U.S. Appl. No. 15/979,011, Notice of Allowance dated Mar. 17, 2021, 26 pgs.

Van Calsteren, "Structure determination of the exopolysaccharide produced by Lactobacillus rhamnosus strains RW-9595M and R", Biochem. J. (2002) 363, 7-17.

D0 (dry skin) — Tension lines

D30 (slightly hydrate skin)

METHODS OF USING COSMETIC COMPOSITIONS COMPRISING EXOPOLYSACCHARIDES DERIVED FROM MICROBIAL MATS

CROSS REFERENCE TO RELATED APPLICATIONS

This application is a Divisional of U.S. patent application Ser. No. 15/979,011 filed May 14, 2018, now issued under no. 11,040,058 on Jun. 22, 2021, which is a Continuation of U.S. patent application Ser. No. 12/988,211 filed Apr. 15, 2009, now abandoned, which is a National Phase Application under 35 U.S.C. § 371 of PCT/CA2009/000493, filed Apr. 15, 2009, and published as WO2009/127057A1 on Oct. 22, 2009, which claims priority, under 35 U.S.C. § 119(e), of U.S. Provisional Application Ser. No. 61/044,992, filed on Apr. 15, 2008, which applications and publication are incorporated herein in their entirety by reference and the benefit of priority of which is claimed herein.

STATEMENT REGARDING FEDERALLY SPONSORED RESEARCH OR DEVELOPMENT

N/A.

FIELD OF THE INVENTION

The present invention generally relates to cosmetic compositions and methods of use thereof.

BACKGROUND OF THE INVENTION

Skin is a physical barrier to the environment. It is the alteration of the barrier properties and actual damage to this barrier that causes skin conditions.

The epidermis and the dermis, separated by the basal membrane, constitute the cutaneous covering on the hypoderm. The epidermis is the most superficial layer of the skin and provides its resistance and impermeability. Alteration of this layer will affect negatively perceived quality of the skin and will lead eventually to cutaneous aging. The dermis, the internal layer of the skin, is conjunctive tissue composed of cells (essentially fibroblasts) dispersed in a complex medium called the extracellular matrix (ECM). This matrix consists of collagen and elastin fibers, glycoproteins (fibronectin and laminin) and proteoglycans. The extracellular matrix serves as a structure for the cells, allowing tissues and organs to cohere in pluricellular organisms.

Cutaneous aging is a complex phenomenon responsible for progressive changes of the skin. Aging of the skin results from two processes: (1) an intrinsic process, corresponding to chronological aging, and (2) an extrinsic process resulting mainly from the deleterious effect of exposure environmental stresses. Genetic, UV exposure, climatic factors (harshness/wind/cold/warm), pollution (chemical, free radicals, contaminant, nitrogen oxide, metals), alcohol consumption or smoking are factors involved in cutaneous aging.

Although different types of cells coexist in the epidermis, keratinocytes make up the majority of this layer and play a role in the resistance provided by the mucocutaneous barrier. They are involved in an extremely precise program of differentiation and maturation, which is subjected to numerous interactions between the epidermal and dermal compartments. The core activity of these cells is the synthesis of keratins, which represent close to 90% of all the protein in the epidermis. The bottom layers of cells adjacent to the dermis are the basal cells which reproduce. As the cell mature, they move towards the outer layer of skin leading to terminal differentiation of the cells. During the process of maturation, the physiology, chemical composition, shape and orientation of the cells change. When the cells reach the top layer of skin—the stratum corneum—the cells are called corneocytes and are no longer viable. Corneocytes lack a nucleus and cellular structures. Corneocytes are flat, hexagonal-shaped cells filled with water-retaining keratin proteins surrounded by a protein envelope and lipids. The cellular shape and the orientation of the keratin proteins add strength to the stratum corneum. There are 10-30 layers of stacked corneocytes. The cells remain connected to each other by protein bridges called desmosomes. Stacked bilayers of lipids surround the cells in the extracellular space. The resulting structure is the natural physical and water-retaining barrier of the skin.

During the process of maturation, the viable cells moving towards the stratum corneum begin to clump proteins into granules. These granules are present in the granular cell layer of the skin and are filled with a protein called filaggrin. Filaggrin becomes complexed with keratin proteins in the granular cells. This complex protects filaggrin from proteolytic breakdown. As the degenerating cells move towards the outer layer of the skin, enzymes break down the keratin-filaggrin complex. Filaggrin is on the outside of the corneocytes, and water-retaining keratin remains inside the corneocytes of the stratum corneum. When the moisture content of the skin is decreased, specific proteolytic enzymes in the stratum corneum are triggered to further break down filaggrin into free amino acids. The free amino acids, along with other physiological chemicals such as lactic acid, urea and salts, are present in the stratum corneum. Together these chemicals are called "natural moisturizing factors" and are responsible for keeping the skin moist and pliable by attracting and holding water property. The water content of the stratum corneum is normally about 30%. The proteolytic breakdown of filaggrin to amino acids only happens when the skin is dry to control the osmotic pressure of the skin and the amount of water it holds. Transglutaminase is an enzyme involved in stratum corneum formation and is a specific marker of differentiation of keratinocytes into corneocytes.

Desquamation is another important factor in keeping the skin smooth. Desquamation is the enzymatic process of dissolving the desmosomes, the protein connections between corneocytes, and the eventual shedding of these cells. Opposite to the production of amino acids from proteolytic degradation of filaggrin proteins, the proteolytic enzymes responsible for desquamation function in the presence of a well-hydrated stratum corneum. These enzymes are located intercellularly. In the absence of water, the cells do not desquamate normally, and the result is thickened, dry, rough, scaly skin.

The last factor that is necessary in explaining how the natural skin barrier works to keep the skin moist and pliable is the function of the intercellular lipids. These lipids form stacked bilayers (multilamellae) surrounding the corneocytes in the stratum corneum and incorporate water into this architecture. The lipids are derived from the degradation of cells in the granular layer of skin (similar to the origin of the protein granules). Special lipid structures called lamellar granules are released into the extracellular spaces of the degrading cells. There is also release of lipids from the former cell membranes. These released lipids include cholesterol, free fatty acids, and sphingolipids. Ceramide, a type of sphingolipid derived from the lamellar granules, is one of the major lipid components responsible for generating the stacked lipid structures. These lipids trap water molecules in their hydrophilic (water attracting) region. The newly formed stacked lipids surrounding the corneocytes provide an impermeable barrier for the passage of water out of the stratum corneum and the prevention of the natural moisturizing factors from leaching out of the surface layers of skin. Lipid layers hold water and surround corneocytes to provide permeability barrier. The intercellular lipids and corneocytes containing proteins and natural moisturizing factors work together to provide an efficient barrier against water loss and water retention to maintain the flexibility of the skin. The protective forces shield the skin from desiccation and environmental assaults. There are sharp decreases in intercellular lipids after age 40 resulting in more susceptibility to dry skin conditions.

Exposure to irritants compromises the barrier function of the stratum corneum and decreases its ability to protect the skin against environmental stresses (e.g., ultraviolet irradiation, infections agents, etc.). Repeated and prolonged exposition to environmental irritants results in denatured skin proteins, disorganization of the lipid lamellae layers, removal of the protective intercellular lipids, loss of natural moisturizing factors and decreased cohesion between cells. These damages are also responsible for the loss of function of the enzymes responsible for desquamation of corneocytes. There is accentuation of these problems with exposure to pollution, cold, sun, wind, low humidity or chemical agents. An irritant is any agent that is capable of producing cell damage if there is exposure for sufficient time and in sufficient concentrations. The severity of the damage is dependent of the type and intensity of exposure to these irritating factors. There are also endogenous factors that make one susceptible to damaged skin by external factors. These factors include having active skin disease such as psoriasis, eczema, inherited dry skin conditions, a previous history of skin disease, sensitive skin and/or older age.

UV exposure is responsible for epidermis and dermis injuries. Solar UVB (290-315 nm) affect essentially the epidermis, whereas UVA (315-400 nm) reach mainly the dermis. Detailed study of histological changes due to UV exposure reveals thickening of the skin, loss of resiliency and decrease in immune functions. Chronic UV radiations cause modification of the dermis biomechanics' properties which make wrinkles appear. Actinic radiance affects epidermis and dermis at different levels. The triggering of elastase process corresponds to the implementation of an abnormal tissue in the upper zone of dermis, which is very characteristic of the chronic action of UVB. This new tissue characterizes itself by a hyperplasia of abnormal elastic fibres and by the occurrence of damaged fibres with the loss of the parallel organization of microfibrils around elastin (KLINGMAN L H, J. Invest. Dermatol 1985-84-272-6).

This process is coupled with an increase of fibres built-up of fibronectin and of fibrillar compounds which are different from elastin. Setting up of such a tissue is responsible for the loss of physical chemistry properties of the dermis. Collagen fibres altered by UVB present themselves as observable dense bundles. UVB radiance whose luminous energy is directly absorbed by the DNA, is mainly leading to changes of the pyrimidic basis.

Therefore, this is a need to develop new approaches for the prevention and/or treatment of skin aging signs and other skin conditions and disorders.

SUMMARY OF THE INVENTION

More specifically, in accordance with the present invention, there is provided a skin care composition comprising at least one exopolysaccharide (EPS) originating from a microbial mat, the EPS being in a concentration of about 0.001% to about 1.5% w/w of the composition.

In a specific embodiment, the microbial mat is a marine microbial mat. In another specific embodiment, the at least one EPS is generated by fermentation of a microorganism isolated from the microbial mat. In another specific embodiment, the at least one EPS comprises at least two EPSS, each EPS originating from different microorganisms isolated from the microbial mat. In another specific embodiment, the at least one EPS comprises at least two EPSS, each EPS originating from different microbial mats. In another specific embodiment, the microbial mat originates from French Polynesia. In another specific embodiment, the at least one EPS is chemically or physically modified. In another specific embodiment, the at least one EPS depolymerized. In another specific embodiment, the at least one EPS is a native EPS. In another specific embodiment, the at least one EPS is sulfated, acetated, lactated, succinated or pyruvated.

In another specific embodiment, the composition of the present invention is for use in anti-aging skin care. In another specific embodiment, the composition of the present invention is for use in after sun skin care. In another specific embodiment, the composition of the present invention is for use in sunscreen skin care. In another specific embodiment, the composition of the present invention is for use for preventing or reducing at least one skin aging sign.

In a specific embodiment, the composition is for improving hydration. In another specific embodiment, the composition is for improving the morphology of stratum corneum. In another specific embodiment, the composition is for improving skin microrelief. In another specific embodiment, the composition is for improving desquamation. In another specific embodiment, the composition is for improving keratinocytes differentiation. In another specific embodiment, the composition is for reducing bacterial adhesion on skin surface. In another specific embodiment, the bacterial strain is *Staphylococcus epidermidis* or *Staphylococcus aureus*. In another specific embodiment, the composition is for stimulating hyaluronic acid production by senescent human fibroblasts. In another specific embodiment, the composition is for stimulating epidermis total lipid synthesis. In another specific embodiment, the composition is for stimulating the expression of at least one gene involved in skin desquamation. In another specific embodiment, the gene is kallikrein 5, neurosin or stratum corneum chymotryptic enzyme. In another specific embodiment, the composition is for stimulating the expression of at least one gene involved in keratinocytes differentiation. In another specific embodiment, the gene is filaggrin, loricrin or involucrin. In another specific embodiment, the composition is for stimulating the expression of transglutaminase. In another specific embodiment, the composition is for reducing intracellular lipid peroxides of irradiated skin cells.

In accordance with another aspect of the present invention, there is provided a use of at least one exopolysaccharide (EPS) originating from a microbial mat, for the manufacture of a skin care composition. In a specific embodiment of the use of the present invention, the skin care composition is an anti-aging skin care composition, an after sun skin care composition or a sunscreen skin care composition.

In accordance with another aspect of the present invention, there is provided a use of at least one exopolysaccharide (EPS) originating from a microbial mat, for preventing or reducing at least one skin aging sign.

In a specific embodiment, the use is for improving hydration. In another specific embodiment, the use is for improving the morphology of stratum corneum. In another specific embodiment, the use is for improving skin microrelief. In another specific embodiment, the use is for improving desquamation. In another specific embodiment, the use is for improving keratinocytes differentiation. In another specific embodiment, the use is for reducing bacterial adhesion on skin surface. In another specific embodiment, the bacterial strain is *Staphylococcus epidermidis* or *Staphylococcus aureus*. In another specific embodiment, the use is for stimulating hyaluronic acid production by senescent human fibroblasts. In another specific embodiment, the use is for stimulating epidermis total lipid synthesis. In another specific embodiment, the use is for stimulating the expression of at least one gene involved in skin desquamation. In another specific embodiment, the gene is kallikrein 5, neurosin or stratum corneum chymotrypsic enzyme. In another specific embodiment, the use is for stimulating the expression of at least one gene involved in keratinocytes differentiation. In another specific embodiment, the gene is filaggrin, loricrin or involucrin. In another specific embodiment, the use is for stimulating the expression of transglutaminase. In another specific embodiment, the use is for reducing intracellular lipid peroxides of irradiated skin cells.

In accordance with another aspect of the present invention, there is provided a method of preventing or reducing a skin aging sign in a subject, comprising administering a composition comprising an effective amount of at least one exopolysaccharide (EPS) originating from a microbial mat on the subject's skin, whereby the skin aging sign is prevented or reduced.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
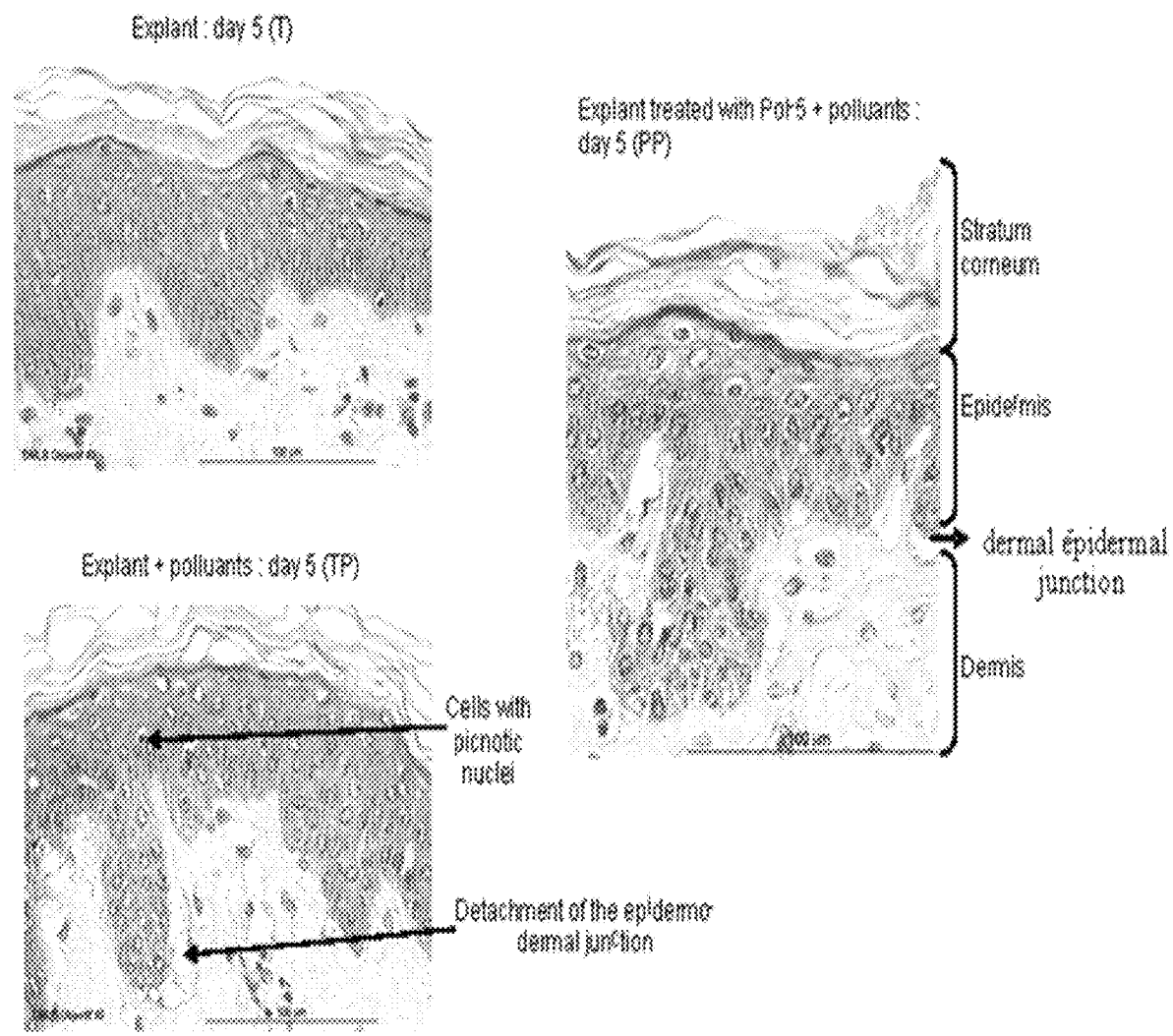
FIG. 1 are photographs of explants at day five after contact with pollutants without EPS treatment (lower left panel) and with EPS treatment (right panel)

Microbial mats develop in a large variety of sites found in coastal areas, such as sandy beaches, marshes, deltas and estuaries, salterns and lagoons. These unique ecosystems are generally constituted of vertically laminated viscous layers produced by the development of different microorganisms. They are subjected to extreme variations of temperature, salinity, acidity and UV rays. Cells of most bacteria are surrounded by mucilaginous external layers essentially constituted of polysaccharides. These layers are more or less attached to the cell surface. Polysaccharides may also be present in the culture medium. These types of polysaccharides are referred to as exopolysaccharides (EPS). (Gautret P, Trichet J. Automicrites in modern cyanobacterial stromatolitic deposits of Rangiroa, Tuamotu Archipelago, French Polynesia: Biochemical parameters underlaying their formation. 2005. *Sedimentary Geology* 178:55-73; Mao Che L, Andréfouët S, Bothorel V, Guezennec M, Rougeaux H, Guezennec J, Deslandes E, Trichet J, Matheron R, Le Campion T, Payri C, and Caumette P. Physical, chemical, and microbiological characteristics of microbial mats (KOPARA) in the South Pacific atolls of French Polynesia. 2001. *Can. J. Microbiol.* 47: 994-101; Richert L, Golubic S, Le Guédés R, Ratiskol J, Payri C, Guezennec J. 2005. Characterization of Exopolysaccharides Produced by Cyanobacteria Isolated from Polynesian Microbial Mats *Current Microbiology* 51: 379-384; Richert L, Golubic S, Le Guédés R, Hervé A, Payri C. Cyanobacterial populations that build 'kopara' microbial mats in Rangiroa, Tuamotu Archipelago, French Polynesia European. 2006. *Journal of Phycology* 41 (3): 259-279).

In French Polynesia microbial mats are growing on the coral reefs of atolls and islets (motu) of some high islands of the Society archipelago. Their thickness depends on locations and environmental conditions and can range from a few millimeters to several tens of centimeters. In the Tuamotu Archipelago these reddish and gelatinous microbial mats are named "Kopara". Years ago, this natural resource was consumed when food was scarce; it seems to be still used for feeding in some archipelagos of the central and North-West Pacific Ocean. It was also employed as healing plaster. Because of some of its properties, especially the nutritional and medical ones, Kopara may be of interest in various fields, e.g., medical and paramedical ones (antibacterial and healing properties), food-industry (carotenoids used as dying agent) and pedology (stabilizers).

Whatever the type of pond where Koparas are found, their structure is quite homogeneous; it consists of a vertically laminated microbial mat. Like most microbial mats it is dominated by some microorganisms characterized by their functional groups: cyanobacteria (those of the genus *Phormidium* along with *Scytonema, Schizothrix* and *Chlorococcales*), sulfurous photosynthetic bacteria such as for example, *Chromatium* and *Thiocapsa*, non-sulfurous red bacteria (PNSB including *Rhodospirillum* and *Rhodopseudomonas/Rhodobium/Blastochloris*) and sulfate reducers (mainly *Desulfovibrio*).

These species have been described partly in literature and although the majority of these species, not pathogenic, belong to known genera, certain species are nevertheless novel. Some of these bacteria, which live and reproduce under extreme conditions, have been found to be able to grow under laboratory culture conditions, to synthesize, and to secrete into the culture medium, a variety of molecules.

More precisely, the present invention relates to the advantageous properties in the cosmetic and dermatology fields of EPS secreted from bacteria originating from microbial mats.

These EPSs are polymers of high molecular weight (typically from about 100,000 Daltons to more than about 5,000,000 Daltons). They consist of chains of various neutral or acid sugars. It is known that some of these EPSs are branched but the structure of others remains unknown.

In Examples below is presented the ability of nine EPS (Pol-1, Pol-2 . . . Pol-9) isolated from microbial mats to stimulate desquamation and improving skin barrier function while maintaining hydration. These EPSs differ chemically one from the other, and are derived from the fermentation of nine distinct species of bacteria from microbial mats originating from French Polynesia. Characteristics of each of these EPSs are provided in Table I below.

Tables II and III below provide molar ratio of various sugars in EPSs Pol-3 and Pal-6, based on Glucose=10.0 for neutral sugars and based on glucuronic acid=10.0 for acid sugars.

TABLE II

| Pol-3 | |
|---|---|
| Neutral sugars | |
| Glucose | 10.0 |
| Galactose | 6.8 |
| Rhamnose | 0.6 |
| Mannose | Traces |
| Fucose | Absent |
| Xylose | Absent |
| Acidic sugars | |
| Glucuronic acid | 10.0 |
| Galacturonic acid | 7.0 |

TABLE I

| | Microorganism | Sugar composition | Substituants | MW | Chelation | Miscellaneous |
|---|---|---|---|---|---|---|
| Pol-1 | | Uronic Acids >35% | Lactate | HMW | Cd, Zn, Pb | |
| Pol-2 | | Uronic Acids close to 25% High level of neutral sugars | Low sulfates level; Acetate; Lactate | HMW | + | Film forming property and Viscosity-increasing property |
| Pol-3 | *Alteromonas macleodii*[1]: *bacillus* Gram- growing at 30° C., saline medium. | Acidic sugars 34% Neutral sugars 60% | Low sulfates level (about 4%) | HMW 380 KDa | ++ | Ramified |
| Pol-4 | | Uronic Acids close to 40% | Low sulfates level | HMW | ++ | Ramified |
| Pol-5 | *Alteromonas macleodii*[2]: *bacillus* Gram- growing at 30° C., saline medium | Uronic Acids close to 25 % Neutral sugars 57% | Sulfate level (8%) | HMW | + Alkali metals and alkaline earth metals | Ramified |
| Pol-6 | *Vibrio alginolyticus*[3]: halophiles | High level of Uronic Acids Acid sugars 12% Neutral sugars 22% | Acetates present Sulfates (0.5%) Phosphates (2.0%) | 720 KDa 3800 KDa | Cd, Zn, Pb | Water retention (hyaluronic acid) |
| Pol-7 | | Majority of neutral sugars | succinates and acetates presence | HMW | | Viscosity-increasing property and gelling property |
| Pol-8 | | Majority of neutral sugars | acetates and pyruvates | | | |
| Pol-9 | | n-acetyl-glucosamine >20% majority of glucose. Also mannose, and glucuronic acid | acetates | | | |

[1]Deposited under the Budapest Treaty on Apr. 21, 2008, at the Collection Nationale de Cultures de Microorganismes (CNCM) (Institut Pasteur, 25 Rue du Docteur Roux, 75724, Paris Cedex 15), under accession No. CNCM I-3970.
[2]Deposited under the Budapest Treaty on Apr. 21, 2008, at the CNCM (Institut Pasteur, 25 Rue du Docteur Roux, 75724, Paris Cedex 15), under accession No. CNCM I-3971.
[3]Deposited under the Budapest Treaty on Jun. 12, 2008, at the CNCM (Institut Pasteur, 25 Rue du Docteur Roux, 75724, Paris Cedex 15), under accession No. CNCM I-4012.

TABLE III

| Pol-6 | |
|---|---|
| Neutral sugars | |
| Glucose | 10.0 |
| Galactose | Absent |
| Rhamnose | 0.7 |
| Mannose | 0.7 |
| Fucose | Traces |
| Xylose | Absent |
| Acidic sugars | |
| Glucuronic acid | 10.0 |
| Galacturonic acid | Absent |

With regards to Pal-5, no substituent was detected on sugar moieties as determined with HPLC and Dionex. Monosaccharides ratios were determined by Gas phase chromatography. D-Glucose: 17.2% (Molar Ratio: 3.2); D-Galactose: 15.3% (MR: 2.9); D-Mannose: 2.6% (MR: 0.5); -D-glucuronic acid 13.0% (MR: 2.0); D-galacturonic acid: 6.4% (MR: 1.0).

The present invention encompasses methods of administering that least one EPS in an effective amount to provide a desired result. In specific embodiments of the present invention, exopolysaccharides of the present invention are used in a concentration between about 0.01 g/L to about 15 g/L in the skin care composition. They may be included in a concentration of 0.001% to about 1.5% w/w of the composition.

The exopolysaccharides of the present invention may be formulated in a topically applicable cosmetic composition (e.g., a topical formulation). Non-limitative examples of such topically applicable compositions include skin care cream, cleansing cream, ointment, skin care lotion, skin care gel, skin care foam, sun care composition, sunscreen skin care, make-up removal cream, make-up removal lotion, foundation cream, liquid foundation, bath and shower preparation, deodorant composition, antiperspirant composition, shaving products composition, after-shave gel or lotion, beauty aids composition, depilatory cream, soap composition, hand cleaner composition, cleansing bar, baby care, hair care, shampoo, setting lotion, treatment lotion, hair cream, hair gel, colouring composition, restructuring composition, permanent composition, anti-hair loss composition, or any other composition which is adapted for the use in a topical cosmetic regimen.

Creams, as is well known in the arts of pharmaceutical and cosmeceutical formulation, are viscous liquids or semi-solid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a non-ionic, anionic, cationic or amphoteric surfactant.

Lotions are preparations to be applied to the skin surface without friction and are typically liquid or semi liquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution may contain other cosmeceutically acceptable chemicals to buffer, stabilize or preserve the solute. Common examples of solvents used in preparing solutions are ethanol, water, propylene glycol or any other cosmeceutically acceptable vehicles.

Gels are semisolid, suspension-type systems. Single-phase gels contain organic macromolecules distributed substantially uniformly throughout the carrier liquid, which is typically aqueous, but also, preferably contain an alcohol, and, optionally, oil. "Organic macromolecules," i.e., gelling agents, are crosslinked acrylic acid polymers such as the "carbomer" family of polymers, e.g., carboxypolyalkylenes that may be obtained commercially under Carbopol™. Other examples are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Ointments are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, no irritating, and no sensitizing. As explained in Remington: The Science and Practice of Pharmacy, 19th Ed. (Easton, Pa.: Mack Publishing Co., 1995), at pages 1399-1404, and ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and, in the present context, encapsulate one or more components of the anti-aging formulations. Liposomal preparations herein include cationic (positively charged), anionic (negatively charged), and neutral preparations. Cationic liposomes are readily available. For example, N[1-2,3-dioleyloxy)propyl]-N,N,N-triethylammonium (DOTMA) liposomes are available under the tradename Lipofectin™ (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphosphatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar head groups form an outer spherical shell, while the hydrophobic, hydrocarbon chains are oriented towards the centre of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Microspheres, similarly, may be incorporated into the present formulations. Like liposomes and micelles, microspheres essentially encapsulate one or more components of the present formulations. They are generally although not necessarily formed from lipids, preferably charged lipids such as phospholipids. Preparation of lipidic microspheres is well known in the art and described in the pertinent texts and literature.

In an embodiment, the composition of the present invention further comprises at least one additional active ingredient/agent. In a further embodiment, the above-mentioned at least one additional active ingredient modulate(s) at least one of cell differentiation, cell metabolic activity, cell structure, cell proliferation, extracellular processes and pigmentation.

The composition of the present invention may further comprise at least one of an agent that modulates cell differentiation or proliferation, an anesthesic agent, anti-acne agent, anti-aging agent, antibacterial agent, anticellulite agent, antifungal agent, anti-inflammatory agent, anti-irritant agent, antioxidant agent, anti-parasitic agent, antipollution agent, antipruritic agent, anti-rosacea agent, anti-seborrhea agent, anti-stress agent, anti-telangiectasia agent, antiviral agent, anti-wrinkle agent, baby care agent, bath and body agent, calming agent, cleansing agent, collagen synthesis agent, elastase inhibitory agent, exfoliant agent, facial peeling agent, firming agent, foot care agent, free radical scavenging agent, immune function modulator agent, keratolytic agent, lift agent, make-up remover agent, melanogenesis stimulator agent, hair care agent, matrix metalloproteinase inhibitory agent, moisturizing agent, oil absorbent agent, osmoregulator agent, anti-photoaging agent, protecting agent, rejuvenating agent, regenerating agent, restructuring agent, sensitive skin agent, shaving product agent, skin defense enhancer agent, skin clarifier agent, skin repair agent, slimming agent, smoothing agent, softening agent, soothing agent, sun care agent, sunless tanning agent, tensing agents and whitening agent, or any other agent adapted for use in a cosmetic regimen that comprises topical application of said cosmetic composition, and which complements or supplements the effect of the EPS of the present invention.

Without being so limited, agents that modulate cell differentiation or proliferation include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), vitamin D and its derivatives (cholecalciferol, ergocalciferol, 25-hydroxycholecalciferol), growth factors, estradiol derivatives. It also includes any combination thereof.

Without being so limited, anaesthetics include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include lidocaine chlorhydrate and its derivatives. It also includes any combination thereof.

Without being so limited anti-acne agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include benzoyl peroxide, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), salicylic acid, sulfur, sulfurated lime, alcohol and acetone. It also includes any combination thereof.

Without being so limited, anti-aging/anti-wrinkle agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include hyaluronic acid, sodium-2-pyrrolidone carboxylate, glycosaminoglycans, kinetin, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, 3-carotene, retinyl ester), epidermal growth factor, ceramide, ethylbisiminomethylguaiacol manganese chloride, glycation inhibitors, *Chrysanthellum indicum* extract and aphanizomenon flos aquae extract. It also includes any combination thereof.

Without being so limited, antibacterial agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include eucalyptus extract, clindamycin phosphate, carvacrol, erythromycin and antibiotics belonging to the group of tetracyclines. It also includes any combination thereof.

Without being so limited, antifungal agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include econazole, ketoconazole, miconazole, amphotericin B, terbinafine and octopirox. It also includes any combination thereof.

Without being so limited, anti-inflammatory agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include allantoin, vitamin E and its derivatives (α-tocopherol, δ-tocopherol, γ-tocopherol), chamomile oil, gingko biloba oil and *Camellia sinensis* extract. It also includes any combination thereof.

Without being so limited, anti-irritant/soothing/smoothing/calming agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include allantoin, *Camellia sinensis* extract, lavender oil, aloe vera, linden extract, *Epilobium angustifolium* extract, chysanthellum indicum extract, *Cola nitida* extract and alteromonas ferment extract. It also includes any combination thereof.

Without being so limited, antioxidant agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include furfuryladenine, panthenol, lipoic acid, ubiquinone, niacinamide, melatonin, catalase, glutathione, superoxide dismutase, polyphenols, cysteine, allantoin, kinetin, vitamin C and its derivatives (ascorbyl palmitate, magnesium ascorbyl phosphate, sodium ascorbyl phosphate), vitamin E and its derivatives (α-tocopherol, δ-tocopherol, γ-tocopherol), grape seed extract and *Camellia sinensis* extract. It also includes any combination thereof.

Without being so limited, antipruritic agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include thenaldine, trimeprazine, and cyproheptadine. It also includes any combination thereof.

Without being so limited, anti-rosacea/anti-telangiectasia agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include metronidazole, vasoconstrictors, benzoyl peroxide, azelaic acid, sulphur, soy proteins and glycosaminoglycans. It also includes any combination thereof.

Without being so limited, anti-seborrhea agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include progesterone derivatives, isoleutrol and hinokitiol. It also includes any combination thereof.

Without being so limited, sensitive skin agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include rose oil and jasmine oil. It also includes any combination thereof.

Without being so limited, cleansing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include ammonium lauryl sulfate, ammonium laureth sulfate, cocamide MEA, triethanolamine lauryl sulfate, sodium stearate and nettle leaf extract. It also includes any combination thereof.

Without being so limited, collagen synthesis agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), vitamin C and its derivatives (ascorbyl palmitate, magnesium ascorbyl phosphate, sodium ascorbyl phosphate), growth factors and its derivatives. It also includes any combination thereof.

Without being so limited, exfoliant agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include alpha/beta hydroxy acids, salicylic acid, glycolic acid, lactic acid, citrus acid and walnut shell powder. It also includes any combination thereof.

Without being so limited, facial peeling agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include glycolic acid, lactic acid, trichloroacetic acid and phenol. It also includes any combination thereof.

Without being so limited, firming/tensing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include dimethylaminoethanol, neuro-cosmetic actives (Botox™-like), chitosan, arnica extract, fennel-sweet oil and papaya extract. It also includes any combination thereof.

Without being so limited, free radical scavenging/antipollution/anti-stress agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include grape seed extract, alpha-tocopherol and the esters thereof, superoxide dismutase, some chelating agents of metals, vitamin C and its derivatives (ascorbyl palmitate, magnesium ascorbyl phosphate, sodium ascorbyl phosphate). It also includes any combination thereof.

Without being so limited, hair care agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include poly-D-glucosamine, poly-N-acetyl-D-glucosamine, stearalkonium chloride and triethanolamine lauryl sulfate. It also includes any combination thereof.

Without being so limited, matrix metalloproteinase inhibitory agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include *Camellia sinensis* extract, polyphenols, spatholobi *caulis* extract, *Euonymus alatus* extract, rhizoma notopterygii extract, quercetin, glycosaminoglycans, polymethoxy flavonoid, N-acetyl-cysteine, 2-furildioxime, isoflavone, vitamin C and its derivatives (ascorbyl palmitate, magnesium ascorbyl phosphate, sodium ascorbyl phosphate), retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester) and hydroxamate derivatives. It also includes any combination thereof.

Without being so limited, moisturizing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include cucumber extract, sodium-2-pyrrolidone carboxylate, sodium PCA, sodium hyaluronate, chitin and its derivatives, alpha hydroxy acids, hyaluronic acid and hydrolysed wheat protein. It also includes any combination thereof.

Without being so limited, osmoregulator agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include mannitol, dulcitol and betaine.

Without being so limited, protecting agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include poly-N-acetyl-D-glucosamine, poly-D-glucosamine, alkyloamides, chitosan, *Chrysanthellum indicum* extract, *Camellia sinensis* extract and alteromonas ferment extract. It also includes any combination thereof.

Without being so limited, rejuvenating agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include rosemary extract, rosewood extract, geranium extract and vitamin E and its derivatives ($\alpha$-tocopherol, $\delta$-tocopherol, $\gamma$-tocopherol). It also includes any combination thereof.

Without being so limited, skin repair agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, 3-carotene, retinyl ester), allantoin, eucalyptus extract, lavender oil, rose oil and activators of collagen synthesis and activators of components of the skin's extracellular matrix. It also includes any combination thereof.

Without being so limited, slimming/anticellulite agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include *Chrysanthellum indicum* extract, dihydromyricetin, theobromine, theophylline, aminophylline, caffeine, isopropylarterenol hydrochloride, epinephrine, $\alpha$-MSH agonists, adenylate cyclase activators and phosphodiesterase inhibitors. It also includes any combination thereof.

Without being so limited, sun care/photo aging agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include PABA (p-aminobenzoic acid) and derivatives, gluconolactone, salicylates, cinnamates, benzophenones, dibenzoylmethanes, oxybenzone, vitamin E and its derivatives ($\alpha$-tocopherol, $\delta$-tocopherol, $\gamma$-tocopherol), ethylbisiminomethylguaiacol manganese chloride, glycosaminoglycans, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), titanium dioxide, octyl methoxycinnamate, benzophenone, octyl salicylate, *Epilobium angustifolium* extract, *Rumex occidentalis* extract, *Chrysanthellum indicum* extract, *Camellia sinensis* extract and alteromonas ferment extract. It also includes any combination thereof.

Without being so limited, sunless tanning/melanogenesis stimulator agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include dihydroxyacetone, $\alpha$-MSH agonists, adenylate cyclase activators and phosphodiesterase inhibitors. It also includes any combination thereof.

Without being so limited, toning agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include nettle extract, orange blossom extract, rosewood extract and witch hazel extract. It also includes any combination thereof.

Without being so limited, whitening/pigmentation agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include arbutin, azealeic acid, vitamin C and its derivatives (ascorbyl palmitate, magnesium ascorbyl phosphate, sodium ascorbyl phosphate), hydroquinone, N-acetyl-4-S-cysteanimylphenol, kojic acid, melanostat (melanostatine), tretinoin, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), ruminex occidentalis extract, licorice, mulberry, arctostaphylos uva-ursi (bearberry), tyrosinase inhibitors, melanosome-transfer inhibitors and melanin scavengers. It also includes any combination thereof.

In an embodiment, the composition of the present invention further comprises a pharmaceutically acceptable topical carrier, vehicle, excipient or additives (i.e. topically/cosmetically acceptable carrier, vehicle, excipient or additives). Such carrier, vehicle, excipient or additives are well known in the art and may be used, for example, to improve final formulation regarding organoleptic properties, skin penetration and accessibility of the active ingredient. Examples of carriers, vehicles or excipients include: buffering agent, carrier agent, chelating agent, conditioner agent, coloring agent, detackifier agent, emollient agent, emulsifier agent, film former agent, foaming agent, humectant agent, lactylate agent, lipophilic agent, lubricant agent, neutralizer agent, oil agent, opacifier agent, preservative agent, solubilizer agent, solvent agent, stabilizer agent, surfactant agent, thickener agent, viscosity agent, water absorbent agent, wetting agent, perfume and thermal water. It also includes any combination thereof.

The composition of the present invention may be formulated so as to provide for a specifically controlled delivery system. Non-limitative examples of such delivery systems include slow delivery system, rapid delivery system, immediate delivery system, delayed delivery system, zero-order delivery system and dual or multiple speed delivery systems. Such controlled delivery systems may be achieved with specific formulations including chemical delivery systems, multiple emulsions, microemulsions, nanoemulsions, encapsulations such as liposomes, microspheres, nanospheres, microsponges, beads and cyclodextrins, polymeric matrices, polymeric cosmetic conjugates, oil body/oleosin, oil-soluble molecular film, skin patches, unit dosages.

Without being so limited, buffering agents are salts of bases/acids, compatible with the nature of the skin and with its pH. Sodium acetate is an example of a frequently used buffer agent.

Without being so limited, carrier agents are ingredients capable of aiding the application of the active ingredient. Isohexadecane is an example of a frequently used carrier.

Without being so limited, chelating agents are ingredients capable of binding mono and divalent cations, such as EDTA, trisodium EDTA, tetrasodium EDTA, disodium EDTA or a combination thereof.

Without being so limited, conditioner agents are ingredients with lubricating action and hydrating effect, such as cetrimonium chloride, dicetyldimonium chloride, trideceth-I2, quaternium-Z7, quaternium-I8, polyquaternium-10, behentrimonium methosulfate, cetearyl alcohol, stearamidopropyl dimethylamine, trimethylsilylamodimethicone, isolaureth-6, octoxynol-4, dimethicone, dimethiconol, cyclopentasiloxane, pareth-7, pareth-9, linoleic acid and glycerin, or a combination thereof.

Without being so limited, detackifier agents are ingredients capable of adsorbing onto tacky materials and reduce their tendency to adhere, such as cyclopentasiloxane, dimethicone and vinyl dimethicone, phenyl trimethicone, isopropyl esters, isostearate esters, dimethyl sebacate and dipropyl sebacate, or a combination thereof.

Without being so limited, emollient agents are ingredients with lubricating action and hydrating effect, such as isopropyl palmitate, sunflower seed oil, mineral oil, stearyl stearate, isopropyl myristate, lanolin, caprylic, capric triglyceride, cyclopentasiloxane, dimethicone, vinyl dimethicone, bis-phenylpropyl dimethicone, alkyl dimethicone, sorbitan stearate, sucrose distearate, myristyl alcohol, myristyl lactate, cetyl acetate, dicaprylyl ether, floraester-20, maleated soybean oil, cyclomethicone, shea butter, hydrogenated coconut oil, isopropyl palmitate, diisostearoyl trimethylolpropane siloxy silicate and alkyl benzoate, or a combination thereof.

Without being so limited, emulsifier agents are ingredients capable of preventing the separation of immiscible substances in an emulsion, of helping to distribute evenly one substance in another, of improving texture, homogeneity, consistency and stability, such as cetearyl alcohol, glyceryl stearate, alkyl acrylate crosspolymer, stearic acid, emulsifying wax, sorbitan oleate, sorbitan stearate, polysorbate, polyethylene glycopolysorbate, triethanolamine, cyclopentasiloxane, dimethicone copolyol, PEG-30 dipolyhydroxystearate, sucrose distearate, PEG-100 stearate, sodium dioctylsulfosuccinate, polyacrylamide, isoparaffin, laureth-7, cetyl phosphate, DEA cetyl phosphate, glycol stearate, stearyl alcohol, cetyl alcohol, behentrimonium methosulfate and ceteareth-2, or a combination thereof.

Without being so limited, film former agents are ingredients capable of forming a dimensionally stable and continuous film to minimize the formula tackiness, such as wheat protein, eicosene copolymer, perfluoromethylisopropyl ether, diisostearoyl trimethylolpropane siloxy silicate, trimethylsiloxysilicate, dimethicone, vinyl dimethicone and cyclopentasiloxane, or a combination thereof.

Without being so limited, foaming agents are ingredients capable of regulating the amount of air in a product, such as lauramide DEA and cocamide MEA, disodium laureth sulfosuccinate, disodium N-octadecyl sulfosuccinamate, ammonium lauryl sulphate, triethanolamine lauryl sulfate, sodium lauryl sulphate and sodium 2-ethylhexylsulfate, or a combination thereof.

Without being so limited, humectant agents are ingredients capable of maintaining constant humidity and retaining moisture, such as glycerine, PEG-8, butylene glycol and propylene glycol, or a combination thereof.

Without being so limited, lubricant agents are ingredients capable of adding slipperiness and reducing friction to improve application, such as dimethicone and dimethicone copolyol, or a combination thereof.

Without being so limited, neutralizer agents are ingredients capable of changing the acid-alkaline balance, such as triethanolamine and sodium hydroxide, or a combination thereof.

Without being so limited, opacifier agents are ingredients capable of changing the look of a clear or translucent product to a creamier or pearlier one, such as glyceryl stearate and PEG-100 stearate, or a combination thereof.

Without being so limited, preservative agents are ingredients capable of retarding or preventing microbial or chemical spoilage and protecting against discoloration, such as DMDM hydantoin, methylparaben, propylparaben, phenoxyethanol, ethylparaben, butylparaben, imidazolidinyl urea, diazolidinyl urea, quaternium-8, quaternium-14, quaternium-15, propylene glycol, dehydroacetic acid, methylchloroisothiazolinone, methylisothiazolinone and germaben, or a combination thereof.

Without being so limited, solubilizer agents are ingredients capable of allowing incompatible ingredients to become part of a homogeneous solution, such as polysorbate, ceteareth, steareth and PEG, or a combination thereof.

Without being so limited, stabilizer agents are ingredients capable of maintaining physical and chemical properties during and after processing, preventing or limiting changes in the physical properties of a substance during product life, such as polyethylene, sodium chloride, stearyl alcohol, xanthan gum, tetrasodium EDTA and dimethicone copolyol, or a combination thereof.

Without being so limited, surfactant agents are ingredients capable of reducing surface tension when dissolved in water or a water solution, reducing interfacial tension between two liquids or between a liquid and a solid, such as sodium dioctylsulfosuccinate, octoxynol-40, isolaureth-6, ammonium lauryl sulfate, lauryl alcohol, lauramide DEA and cocoamidopropyl betaine, or a combination thereof.

Without being so limited, thickener agents are ingredients capable of absorbing water to impart body, improve the consistency or texture, and stabilize an emulsion, such as stearic acid, magnesium aluminum silicate, carbomer (including sodium carbomer and potassium carbomer), alkyl acrylate crosspolymer, polyacrylamide, isoparaffin, laureth-7, cetyl alcohol, xanthan gum, alkyl dimethicone, hydroxyethylcellulose, glyceryl stearate, pentaerythrityl tetrastearate, stearyl alcohol and polyquaternium-10, or a combination thereof.

Without being so limited, viscosity agents are ingredients capable of controlling the degree of fluidity and the internal resistance to flow exhibited by a fluid, such as magnesium aluminium silicate, caprylyl glycol and myristyl alcohol, or a combination thereof.

Without being so limited, water absorbent agents are ingredients capable of absorbing the product's water to maintain the moisture, such as carboxyvinyl polymer, acrylic copolymer, polyacrylamide, polysaccharides, natural gum, clay, modified clay, metallic salt, fatty acid, or a combination thereof.

Without being so limited, wetting agents are ingredients capable of reducing the surface tension of the water for better penetration or spread over the surface, such as caprylate, caprylyl glycol, glyceryl caprate, polyglyceryl-2 caprate, polyglyceryl-6, polyglyceryl-3 laurate and TEA-laureth sulfate, or a combination thereof.

The exopolysaccharides or compositions of the present invention may be packaged in any suitable manner, including but not limited to, a jar, a bottle, a tube, a stick, a roller-ball applicator, an aerosol spray device, etc., in the conventional manner. The exopolysaccharides or compositions of the present invention could be packaged as a kit of two or more separate compartments, including one containing the active ingredients and a second containing a topically/dermatologically-acceptable vehicle, which may be mixed together at some fixed time point prior to application. For example, the active ingredients, in the form of a cream, a powder, a tablet, a capsule or a liquid, may be contained in sealed, single-use packets, which may be opened and mixed with the topically-acceptable vehicle, which may also be stored in pre-measured form in sealed, single-use packets. Alternatively, the active ingredients and the topically-acceptable vehicle may be provided in larger quantities from which the needed amount could be withdrawn using various measuring devices, such as a measuring spoon or cup for solids, or a calibrated vial or dropper for liquids. The exopolysaccharides or compositions of the present invention may be spread onto a substrate and then subsequently packaged. Suitable substrates include dressings, including film dressings, and bandages. In an embodiment, the kit or package may comprise instructions for use/application, e.g., instructions for preventing or reducing a skin condition or a skin aging sign.

In another aspect, the present invention provides the use (e.g., cosmetic or therapeutic use) of exopolysaccharides for preventing or reducing a skin aging sign or another skin condition in a subject.

In another aspect, the present invention provides the use (e.g., cosmetic or therapeutic use) of exopolysaccharides for preventing or reducing a skin aging sign. Without being so limited, as used herein, the terms "skin aging sign" refers to wrinkles, fine lines, loss of skin firmness and elasticity, loss of texture, dehydration, as weakening of skin defense mechanism, inflammation, sun damage (particularly UV radiation-induced oxidative stress), redness, telangiectasia, skin sagging, excess sebum, enlarged pores, dark circles, loss of skin firmness, brown spot, age spots, hyper pigmented skin, increased skin thickness, blemishes, loss of skin elasticity and collagen content, dry skin, lentigines, melasmas, dull skin, bags under eyes, disturbance of sebum production, loss of skin comfort and skin devitalization (reduced metabolic activity), or any combination thereof.

As used herein, the terms "reducing" in the expression "reducing skin aging sign" or "reducing skin condition or disorder" is meant to refer to a reduction of a pre-existing aging skin sign, or skin condition or disorder, respectively. It encompasses complete or partial correction/treatment of the aging sign or skin condition or disorder, respectively. As used herein, the term "preventing" in the expression "preventing skin aging sign" or "preventing skin condition or disorder" is meant to refer to a delay in the initiation of, or a complete or partial prevention of a skin aging sign, or skin condition or disorder, respectively.

As used herein, the terms "originating from a microbial mat" as it relates to an EPS are meant to refer to the origin of the microorganism secreting the EPS. An EPS secreted by a microorganism strain cultivated in vitro from a strain originally isolated from a microbial mat is also encompassed by the terms "originating from a microbial mat". Similarly, the terms "microorganism isolated from a microbial mat" encompass a microorganism strain cultivated in vitro from a strain originally isolated from a microbial mat. It also includes recombinant microorganisms that contain the gene encoding the EPS.

In another aspect, the present invention relates to the use of exopolysaccharides for improving the consistency of skin by cells attrition, desquamation and improvement of collagen fibres structure.

In another aspect, the present invention relates to the use of exopolysaccharides for improving the morphology of stratum corneum.

In another aspect, the present invention relates to the use of exopolysaccharides for improving desquamation.

In another aspect, the present invention relates to the use of exopolysaccharides for reduction of bacterial adhesion on skin surface.

In another aspect, the present invention relates to the use of exopolysaccharides for improving hydration.

In another aspect, the present invention relates to the use of exopolysaccharides for improving skin microrelief.

In another aspect, the present invention relates to the use of exopolysaccharides for stimulating hyaluronic acid production by senescent human fibroblasts.

In another aspect, the present invention relates to the use of exopolysaccharides for stimulating epidermis total lipid synthesis.

In another aspect, the present invention relates to the use (e.g., cosmetic use) of exopolysaccharides for stimulating the expression of genes involved in the desquamation function. In a further embodiment, the above-mentioned genes are coding for KLK5 (kallikrein, stratum corneum enzyme), KLK6 (neurosin) and KLK7 (stratum corneum chymotrypsic enzyme).

In another aspect, the present invention relates to the use (e.g., cosmetic use) of exopolysaccharides for stimulating the expression of genes involved in keratinocytes differentiation. In a further embodiment, the above-mentioned genes are coding for filaggrin and involucrin.

In another aspect, the present invention relates to the use (e.g., cosmetic use) of exopolysaccharides for stimulating the expression of transglutaminase.

In another aspect, the present invention provides the use of exopolysaccharides for the preparation of a medicament for preventing or reducing a skin condition or skin aging sign.

In another aspect, the present invention provides the use of exopolysaccharides for the preparation of a medicament for improving the consistency of skin by cells attrition, desquamation and improvement of collagen fibres structure.

The aging-related skin condition may in more specific embodiments, involve wrinkles, fine lines, age spots, sun damage (particularly UV radiation-induced oxidative stress), blemishes, hyper pigmented skin, age spots, increased skin thickness, loss of skin elasticity and collagen content, dry skin, lentigines, and/or melasmas or any combination thereof.

The method of delivery of exopolysaccharides or compositions of the present invention may vary, but usually involves application to an area of skin prone to, or affected by, a skin aging sign, e.g., any skin sign associated with, caused by, or affected by, intrinsic aging and/or extrinsic aging.

A cream, lotion, gel, ointment, paste or the like may be spread on the affected surface and gently rubbed in. A solution may be applied in the same way, but more typically will be applied with a dropper, swab, or the like, and carefully applied to the affected areas.

The application regimen will depend on a number of factors that may readily be determined, such as the severity of the condition and its responsiveness to initial treatment, but will normally involve one or more applications per day on an ongoing basis. One of ordinary skill may readily determine the optimum amount of the formulation to be administered, administration methodologies and repetition rates. In general, it is contemplated that the formulations of the invention will be applied in the range of once or twice weekly up to once or twice daily. Hence as used herein the terms "effective amount" as they relate to a composition of the present invention is an amount that effectively prevents or reduces a skin aging sign or a skin condition or disorder of the subject. It typically constitutes an amount sufficient to cover the skin that is to be treated. The effective amount may vary depending on the form of the composition (e.g., gel, cream, serum, etc.) and the type of skin of the subject.

In an embodiment, the above-mentioned subject is a mammal. In a further embodiment, the above-mentioned mammal is a human.

The present invention is illustrated in further details by the following non-limiting examples.

Example 1

Effect of EPS on Human Keratinocytes (Viability In Vitro)

The cytotoxicity evaluation of each EPS was performed by using the MTT assay in order to determine the concentrations which are not harmful to human keratinocytes (NHEK, 3rd passage).

The MTT Cell Proliferation Assay measures the cell proliferation rate and conversely, when metabolic events lead to apoptosis or necrosis, the reduction in cell viability. The assay is based upon the capacity of the mitochondrial dehydrogenase to reduce the yellow tetrazolium MTT (3-(4, 5-dimethylthiazolyl-2)-2, 5-diphenyltetrazolium bromide), to generate reducing equivalents such as NADH and NADPH. The resulting intracellular purple formazan can be solubilised and quantified by spectrophotometric means. The results are given in Table IV below.

TABLE IV

| EPS preparation | Concentration (mg/mL) | Cell's viability % of MTT conversion |
| --- | --- | --- |
| Pol-1 | 0.056 | 98 |
|  | 0.018 | 102 |
|  | 0.006 | 98 |
| Pol-2 | 0.111 | 97 |
|  | 0.037 | 103 |
|  | 0.012 | 101 |
| Pol-3 | 0.037 | 95 |
|  | 0.012 | 97 |
|  | 0.004 | 101 |
| Pol-4 | 0.056 | 95 |
|  | 0.018 | 101 |
|  | 0.006 | 98 |
| Pol-5 | 0.037 | 105 |
|  | 0.012 | 104 |
|  | 0.004 | 104 |
| Pol-6 | 0.111 | 99 |
|  | 0.037 | 94 |
|  | 0.012 | 94 |
| Pol-7 | 0.056 | 104 |
|  | 0.018 | 101 |
|  | 0.006 | 102 |
| Pol-8 | 0.056 | 87 |
|  | 0.018 | 91 |
|  | 0.006 | 96 |
| Pol-9 | 0.012 | 100 |
|  | 0.004 | 101 |
|  | 0.001 | 108 |

No viability alteration was observed at the polysaccharide concentrations tested in this assay.

Example 2

Effect of EPS on Senescent Human Fibroblasts (Viability In Vitro)

The cytotoxicity evaluation of each compound was performed by using the MTT assay as described in Example 1 above, in order to determine the concentrations which are not harmful to senescent human fibroblasts. These senescent cells were obtained by subcultures of normal dermal fibroblasts and a senescent phenotype was obtained from the 12th passage. Table V below provide viability results.

TABLE V

| EPS preparation | Concentration (mg/mL) | Cell's viability % of MTT conversion |
|---|---|---|
| Pol-1 | 0.167 | 101 |
|  | 0.056 | 104 |
|  | 0.018 | 108 |
| Pol-2 | 0.333 | 99 |
|  | 0.111 | 107 |
|  | 0.037 | 104 |
| Pol-3 | 0.333 | 102 |
|  | 0.111 | 105 |
|  | 0.037 | 105 |
| Pol-4 | 0.500 | 112 |
|  | 0.166 | 118 |
|  | 0.055 | 117 |
| Pol-5 | 0.333 | 104 |
|  | 0.111 | 116 |
|  | 0.037 | 117 |
| Pol-6 | 0.111 | 94 |
|  | 0.037 | 95 |
|  | 0.012 | 93 |
| Pol-7 | 0.167 | 104 |
|  | 0.055 | 100 |
|  | 0.018 | 100 |
| Pol-8 | 0.500 | 99 |
|  | 0.166 | 112 |
|  | 0.055 | 112 |
| Pol-9 | 0.111 | 105 |
|  | 0.037 | 102 |
|  | 0.012 | 95 |

No viability alteration was observed at the polysaccharide concentrations tested in this assay.

Example 3

Effect of EPS on Hyaluronic Acid Synthesis by Senescent Human Fibroblasts

This study has been performed in order to evaluate the effects of the EPSs on the synthesis of hyaluronic acid by senescent human fibroblasts. Hyaluronic acid synthesis is a marker of fibroblasts activity and this compound is a natural skin humectant, as it possesses hygroscopic properties. These senescent cells are obtained by subcultures of normal dermal fibroblasts and a senescent phenotype is obtained from the 12th passage.

Gene expression analysis of EPSs tested demonstrated a decrease of synthesis of extracellular matrix proteins, a decrease in sensitivity to growth factors, and an increase of synthesis of matrix metalloproteinases. Some compounds having no direct effect on cell growth have been demonstrated to stimulate proliferation of senescent fibroblasts in presence of epidermal growth factor (EGF). This effect was attributed to an increase in sensitivity of cells to EGF. Based on this observation for EGF, a similar situation could exist for other factors like TGFβ. TGFβ has the ability to trigger HA synthesis. It has been observed however, that older cells become desensitized to TGFβ. Two types of effects of EPSS have thus been tested: their direct effect on the production of HA and their possibility to restore sensitivity of the cells to TGFβ.

Senescent fibroblasts were pre-cultivated for 24 hours until confluence. Then, the culture medium was removed and replaced by assay medium containing or not (control), the tested EPSS alone, TGFβ alone or the mix of tested EPSS with TGFβ. The cells were then cultivated for 72 hours. At the end of the incubation, the hyaluronic acid concentration was evaluated in the supernatant by a standard ELISA assay according to the manufacturer's procedures (R&D Systems DY3614) and cell viability was evaluated by using a standard MTT incorporation assay. The results are given in Table VI below.

TABLE VI

| Treatment | Concentration (g/L) | HA (µg/ml) | % of control |
|---|---|---|---|
| Culture without TGFβ | | | |
| Control | — | 2.48 | 100 |
| TGFβ | $1.10^{-5}$ | 11.73 | 473 ** |
| Pol-2 | 0.333 | 4.05 | 163 * |
|  | 0.111 | 3.81 | 154 |
|  | 0.037 | 3.50 | 141 |
| Pol-3 | 0.333 | 5.67 | 228 ** |
|  | 0.111 | 4.79 | 193 ** |
|  | 0.037 | 3.03 | 122 |
| Culture with TGFβ | | | |
| TGFβ | $1.10^{-5}$ | 16.05 | 100 |
| Pol-5 with TGFβ 10 ng/mL | 0.333 | 10.93 | 68 * |
|  | 0.111 | 12.09 | 75 |
|  | 0.037 | 15.51 | 97 |
| Pol-7 with TGFβ 10 ng/mL | 0.167 | 6.44 | 49 ** |
|  | 0.055 | 7.34 | 56 ** |
|  | 0.018 | 11.26 | 86 |
| Pol-8 with TGFβ 10 ng/mL | 0.500 | 6.07 | 46 ** |
|  | 0.166 | 7.18 | 55 ** |
|  | 0.055 | 10.04 | 77 |
| Pol-9 with TGFβ 10 ng/mL | 0.111 | 7.88 | 60 ** |
|  | 0.037 | 9.45 | 72 * |
|  | 0.012 | 9.42 | 72 ** |

The TGFβ at 10 ng/ml has clearly and significantly increased the hyaluronic acid synthesis (4 folds).

The compound Pol-3 without TGFβ significantly increased, with a dose response, the production of hyaluronic acid (HA). The compound Pol-2 presents the same effects as the product Pol-3, but with a weaker activity.

The compounds Pol-5, Pol-7, Pol-8 and Pol-9 did not have any effect on the basal HA production but significantly decreased the stimulating effect of TGFβ on HA production.

The results obtained with products Pol-5, Pol-7, Pol-8 and Pol-9 suggest a binding with the receptor, but with an antagonistic effect because they decrease the response to TGFβ.

Example 4

Effect of EPSS on the Production of Lipid Peroxides in Human Cell Culture Exposed to UV Irradiation This study was performed to evaluate the effect of EPSs of the invention on the relative quantification of the amount of lipid peroxides (LP) (degradation of skin lipids) in human cells exposed or not to UVA+UVB irradiation. The evaluation was obtained by using a specific fluorescent probe and fluorescence flow cytometry analysis. This method offers a great sensitivity because the fluorescence of each cell is measured and numerous cells are evaluated (10000 cells per experimental condition).

Keratinocytes were pre-cultivated in complete SFM medium up to 100% of confluence. The culture medium was then replaced with assay medium containing or not the tested EPSS or the reference and the cells were incubated at 37° C. and 5% $CO_2$ for 24 h. After incubation, a specific probe, fluorescent analogue of lipids (C11-Fluor) and the tested EPS or the references were incorporated and the cells were incubated at 37° C. and 5% $CO_2$ for 45 minutes. The probe was then eliminated by rinsing with culture medium. The washing medium was replaced with culture medium containing the tested EPSs or the references. Untreated controls were carried out in parallel. The cells were irradiated at 210 mJ/cm² UVB. Non-irradiated controls were carried out in parallel. After irradiation, the cells were incubated for 1 h at 37° C. and 5% CO₂, then rinsed with PBS and trypsinated. The fluorescence parameters were measured by flow cytometry with a FACSArray™ cytometer driven by the FACSArray™ system software (Becton-Dickinson) on 10 000 individual cells (no cell population selection). In this assay, the fluorescent probe C11-Fluor inserted in membrane cells, decreased upon oxidation. The results are given in Table VII below.

TABLE VII

| Treatment | Concentration (mg/mL) | % protection |
|---|---|---|
| Control + UVB | / | 0 |
| Control − UV | / | 100** |
| BHA | 50 µM | 76** |
| Pol-5 | 0.037 | 18* |
|  | 0.012 | 28* |
|  | 0.004 | 24 |

The irradiation increased significantly the amount of intracellular lipid peroxides (7 folds). The reference BHA at 50 µM reduced the amount of intracellular lipid peroxides of irradiated cells (76% of protection). This result was expected and validated the assay.

The compound Pol-5 has a tendency to reduce the amount of intracellular lipid peroxides of irradiated cells.

Example 5

Effects of EPSS on the Expression of Genes Coding for Proteases Involved in Desquamation and Markers of Differentiation in Cultures of Human Keratinocytes This assay was performed in order to measure the effects of the EPSs on the induction of mRNA coding for differentiation proteins (filaggrin, loricrin, involucrin) and for stratum corneum tryptic enzyme involved in desquamation (kallikrein 5, 6 and 7). The relative expression of the selected markers was assayed using the "real time quantitative polymerase chain reaction" technology (RT-QPCR).

Keratinocytes were pre-cultivated in culture medium. At confluence, the culture medium was changed into assay medium (SFM without EGF and pituitary extract) containing or not (control) the test compound and the cells were incubated for 24 h at 37° C. and 5% CO2. At the end of the experiment, the cells were washed in PBS buffer and immediately frozen at −80° C. with 300 µl per well of Tri-reagent.

Primers couples allowing the amplification of a specific Polymerase Chain Reactions (PCR) product from each selected marker were used: Liver glyceraldehyde 3-phosphate dehydrogenase (G3PDH) was used as a reference marker in this experiment. The total RNA extraction was performed by Tri-Reagent™ according to the protocol. The elimination of contaminant DNA was performed by DNAse treatment using the "DNA-free" system. Reverse-transcription of mRNA in the presence of oligo(dT) and Superscript II reverse transcriptase was then performed.

Initially, the modulation of gene expression was evaluated on six EPSs at the first concentration (Table VIII). As a second step, it was evaluated on four EPSs at three concentrations (Table IX).

TABLE VIII

| Treatment | Concentration (g/L) | Proteases involved in desquamation | | | Proteins differentiation | | |
|---|---|---|---|---|---|---|---|
|  |  | KLK5 | KLK6 | KLK7 | INV | FLG | LOR |
| Control | — |  |  |  |  |  |  |
| Retinoic acid | 10⁻⁷M | 100 | 100 | 100 | 100 | 100 | 100 |
|  |  | 146 | 315 | 268 | 79 | 35 | 29 |
| CaCl₂ | 1.5 mM | 207 | 110 | 291 | 282 | 125 | 98 |
| Pol-1 | 0.056 | 110 | 82 | 70 | 152 | 47 | 96 |
| Pol-2 | 0.111 | 109 | 80 | 103 | 129 | 75 | 76 |
| Pol-3 | 0.037 | 121 | 79 | 105 | 148 | 174 | 96 |
| Pol-4 | 0.056 | 65 | 99 | 78 | 115 | 60 | 58 |
| Pol-5 | 0.037 | 105 | 110 | 78 | 178 | 61 | 94 |
| Pol-6 | 0.111 | 235 | 1247 | 686 | 480 | 372 | 234 |

TABLE IX

| Treatment | Concentration (g/L) | Proteases involved in desquamation | | | Proteins differentiation | | |
|---|---|---|---|---|---|---|---|
|  |  | KLK5 | KLK6 | KLK7 | INV | FLG | LOR |
| Control | — | 100 | 100 | 100 | 100 | 100 | 100 |
| Pol-2 | 0.111 | 109 | 117 | 102 | 140 | 87 | 125 |
|  | 0.033 | 94 | 109 | 101 | 160 | 109 | 222 |
|  | 0.011 | 98 | 108 | 100 | 144 | 126 | 69 |
| Pol-3 | 0.037 | 101 | 116 | 131 | 173 | 221 | 170 |
|  | 0.0123 | 57 | 96 | 114 | 113 | 157 | 64 |
|  | 0.0041 | 54 | 102 | 114 | 96 | 130 | 31 |
| Pol-5 | 0.037 | 86 | 113 | 135 | 165 | 64 | 92 |
|  | 0.0123 | 82 | 107 | 90 | 157 | 106 | 94 |
|  | 0.0041 | 71 | 83 | 87 | 139 | 98 | 145 |
| Pol-6 | 0.111 | 319 | 1284 | 988 | 491 | 591 | 233 |
|  | 0.033 | 160 | 380 | 407 | 236 | 203 | 61 |
|  | 0.011 | 103 | 102 | 153 | 107 | 93 | 72 |

Retinoic acid showed a reverse differencing profile. CaCl₂ showed a pro differentiation profile. These results were expected and validated the assay.

Pol-6 showed a strong increased of genes coding for desquamation and differentiation. This exopolysaccharide induces cell keratinocytes differentiation to corneocytes (pro differencing effect).

The second series of test showed that Pol-3 presents a pro differencing profile.

Example 6

Effects of EPSS on the Epidermal Lipid Synthesis

Evaluation on Phospholipids and Neutral Lipids Synthesis in Reconstructed Epidermis This study was performed to evaluate the effect of EPSs of the invention on lipid synthesis. Phospholipids (cellular membranes) and neutral lipids (including epidermis specific lipids) were measured separately using thin layer chromatography. SkinEthic™ reconstructed human epidermis was used for model, its composition being close to normal human epidermis.

The epidermal tissues were placed in 24-well plates and cultivated for 12 h in SkinEthic™ medium. The medium was then replaced by fresh medium and the tested EPSS were applied on the surface of epidermis (topical treatment), at the indicated concentrations. Three control epidermises were untreated and three reference epidermises were treated with the retinoic acid, a known stimulant of total skin lipids, in the culture medium (systemic treatment). All treatments were performed in triplicate and cultivated for 72 hours in total. After 24 h treatment, the culture medium was replaced by labelling medium (0.225 µCi/wells of [14C] acetate) and the epidermises were treated. The labelling was carried out during a 48-hour incubation period. The Radioactive marker used was [2-14C]-Acetic acid sodium salt, Amersham CFA14 (2.04 Gbq/mmol, 55 mCi/mmol). The epidermises were washed in PBS solution and were dissociated. Then, cells were lysed by treatment with perchloric acid at 0.5 M on ice. Lipids were extracted by methanol/chloroform (2:1) and phase separation was performed by addition of PBS and chloroform after neutralisation in accordance with the procedure described by Bligh and Dyer. The radioactivity was quantified by incorporation into organic phase (lipids) with liquid scintillation (LKB 1210 Rackbeta) after chloroform evaporation. The organic phases were dried under nitrogen and thin layer chromatography (TLC; plates Merck K60) was performed by using two solvent systems: chloroform/methanol/water for Phospholipids (50:18:2.6) or hexane/ether/acetic acid for Neutral lipids (15:5.6:0.19). The various metabolites were quantified by performing a direct count of the radioactivity of the various spots on TLC plates with PhosphorImager Cyclone™ and Multigauge software (Fujifilm). The results are given in Table X below.

TABLE X

| Treatment | Concentration (g/L) | % Control | | | | | | | |
|---|---|---|---|---|---|---|---|---|---|
| | | TL | C | FFA | EFA | SM | PL | $CSO_4$ | Cera/Cere |
| Control | — | 100 | 100 | 100 | 100 | 100 | 100 | 100 | 100 |
| Retinoic acid | $10^{-6}$M | 175** | 77* | 76 | 133 | 106 | 105 | 92 | 85* |
| Pol-1 | 0.168 | 77 | 112 | 104 | 116 | 82** | 89 | 83* | 97 |
| Pol-2 | 0.333 | 118 | 105 | 103 | 154 | 83** | 89* | 99 | 82* |
| Pol-3 | 0.111 | 165** | 73 | 93 | 81** | 97 | 104 | 109* | 76* |
| Pol-4 | 0.168 | 176** | 75 | 89* | 63** | 110* | 116** | 116** | 77* |
| Pol-5 | 0.111 | 157* | 85 | 79 | 117* | 89* | 105 | 90 | 83* |
| Pol-6 | 0.333 | 183** | 68 | 84* | 67* | 111 | 113* | 104 | 83* |
| Pol-7 | 0.168 | 174** | 62 | 81* | 10** | 116** | 109 | 129** | 94 |
| Pol-8 | 0.168 | 159** | 71 | 144** | 30* | 102 | 96 | 123** | 89 |
| Pol-9 | 0.037 | 127 | 76 | 70* | 31** | 84* | 102 | 87 | 104 |

Lipid synthesis:
Total Lipids (TL)
Cholesterol (C)
Free Fatty Acids (FFA)
Esterified Fatty Acids (EFA)
Sphingomyelin (SM)
Phospholipids (PL)
Sulfate Cholesterol (CS04)
Ceramides and cerebrosides (Cera/Cere)

The basal incorporation of 14C-Acetate in the epidermal lipids was strong, revealing that the metabolism of epidermal keratinocytes was normal.

The reference retinoic acid significantly increased the synthesis of total lipids (175% of control) as expected.

The EPSs Pol-3, Pol-4, Pol-5, Pol-6, Pol-7 and Pol-8 have significantly increased the synthesis of total lipids (165%, 176%, 157%, 183%, 174% and 159% of the control, respectively). The compounds Pol-1, Pol-2 and Pol-9 did not however significantly modify the synthesis of totals lipids.

Example 7

Effect of EPSS on *Staphylococcus Epidermidis* and *Staphylococcus Aureus* Adhesion on Human Skin Surface This study was carried out to evaluate the activity of the EPSs on the adhesion of the biotin-tagged bacteria (*Staphylococcus epidermidis* and *S. aureus*) on human skin surface.

Pieces of human skin (4 cm×4 cm) were prepared from an abdominal biopsy removed from a healthy subject during cosmetic reductive surgery.

*S. epidermidis* and *S. aureus*, the bacteria strains used in this experiment, have the properties to adhere to any support as this was demonstrated on biomaterials, catheters and on various cells. The bacteria were seeded in LB-agar medium, then cultivated at 37° C. in LB liquid medium until semi-log phase (D0640=0.4). The bacteria were then fixed in ethanol 70%, washed and biotin-tagged. The purified bacteria partially biotin-tagged were aliquoted and frozen at −80° C. before use.

One 96 wells-plate was prepared with the skin. Tested EPSS were applied for 1 hour. At the end of incubation, the EPSs were removed and the skin was put in contact with *S. epidermidis* or with *S. aureus*. After 2 hours of incubation at room temperature and 3 washes in PBS, guanidine 4 M was added in each well and left for 40 minutes at room temperature. The supernatant was then extracted and frozen at −80° C.

A sample of each supernatant and each bacterium were transferred on a nitrocellulose membrane (Hybond™, ECL, Amersham), using a MilliBlot dotblot device (Millipore). All controls were performed to evaluate the specificity of the final response. A control of interference with the detection system was performed by transferring culture medium or tested compounds on the nitrocellulose membrane without previous contact with bacteria or skin. No interference was observed in this assay. Non-specific sites on membranes were saturated for 2 h, at 37° C., in a saturation buffer PBS/0.05% Tween 20/5% fat free milk (PBS™). After extensive washing in PBS™, the specific antigenic sites were labelled with Streptavidin-horseradish peroxidase conjugate diluted in PBS™. After extensive washing in PBS™, the peroxidase activity was revealed using the chemiluminescence ECL method (enhanced chemiluminescence, Amersham) on Kodak™ MR film. The results are given in Table XI below.

TABLE XI

| Treatment | Concentration | % of control | % inhibition |
|---|---|---|---|
| Bacterial adhesion of S. epidermidis | | | |
| Control | — | 100 | 0 |
| Pol-1 | 1.8 g/L | 62** | 38 |
| Pol-5 | 0.9 g/L | 35** | 65 |
| Bacterial adhesion of S. aureus | | | |
| Control | — | 100 | 0 |
| Pol-1 | 1.8 g/L | 51* | 49 |
| Pol-5 | 0.9 g/L | 44** | 66 |

The S. epidermidis bacteria adhesion was significant and the signal amplitude was satisfactory. The compounds Pol-1 and Pol-5 significantly decreased the adhesion of S. epidermidis to the skin (respectively 38% and 65% of inhibition).

The S. aureus bacteria adhesion was significant, and the signal amplitude was satisfactory. The compounds Pol-1 and Pol-5 significantly decreased the adhesion of S. aureus to the skin (respectively 49% and 66% of inhibition).

In conclusion, the compounds Pol-1 and Pol-5 exhibit properties able to create a film or mask protecting from the adhesion of the bacteria S. epidermidis or S. aureus on the surface of human skin.

Example 8

Effects of an EPS Formulation Cream on Antipollution Activity

This study was performed to evaluate the antipollution activity of a cosmetic product though its effect against free radicals on normal skin. A mixture of pollutants and heavy metals was used to mimic the harmful effects of an environmental pollution (like fumes, smoke . . . ). Explants were used as a skin model in this experiment as a good model of human skin.

Pieces of human skin (27 explants) were prepared from an abdominal biopsy removed from a healthy subject (64 years old) during cosmetic reductive surgery. They were placed in BEM medium at 37° C. and 5% $CO_2$ The tested EPSS were applied on the surface of epidermis (topical treatment) at the indicated concentrations (2 mg per explant). They were applied the first day (Day 0) and after one, two, three and four days (Day 1, Day 2, Day 3 and Day 4).

At Day 4, 30 μL of a mixture of heavy metals (Table XII) and hydrocarbon was applied on a paper disk and immediately placed on identified explants.

TABLE XII

| Heavy Metals used for the mixture | Concentration (mg/L) |
|---|---|
| Aluminum | 20 |
| Arsenic | 20 |
| Lead | 20 |
| Chromium | 20 |
| Mercury | 20 |
| Nickel | 5 |
| Cadmium | 2 |

At Day 0 and Day 5, 3 explants of each batch were removed and fixed in Bouin's liquid for morphological observation. After 48 hours in Bouin medium, explants were dehydrated, embedded in paraffin and stained in Masson's Trichrome. The MDA assay (Malondialdehyde, a stable product from the radical alteration) was performed in culture medium of Day 3, 24 h after irradiation to quantify the efficiency of products against free radicals generated by pollutants. The results are given in Table XIII below.

Explants without treatment (T), Day 5: the stratum corneum was thick, slightly laminated, clearly keratinised on surface and slightly keratinized at its base. Parakeratosis was moderate. The epidermis had 4 to 5 cellular layers with a good morphology. The relief of dermal-epidermal junction was clear. Papillary dermis indicated thick collagen fibres forming a more or less compact meshwork. See FIG. 1, upper left panel.

Explants with pollutants (TP), Day 5: the stratum corneum was thick, slightly laminated, clearly keratinised on surface. Parakeratosis was moderate. The epidermis had 4 to 5 cellular layers with deep alterations. These alterations were characterised by the presence of many cells with picnotic nuclei throughout epidermis. Detachment of the dermal-epidermal junction was clear. Its relief was rather clear. Papillary dermis indicated thick collagen fibres forming a not very compact meshwork. See FIG. 1, lower left panel.

Explants with pollutants, treated with Pol-5 (PP), Day 5: the stratum corneum was thick, slightly laminated and clearly keratinised on surface. Parakeratosis was moderate. The epidermis had 4 to 5 cellular layers with few alterations. Detachment of the dermal-epidermal junction was light. The relief of dermal-epidermal junction was rather clear. Papillary dermis indicated thick collagen fibres forming a not much compact meshwork. See FIG. 1, right panel.

TABLE XIII

| Treatment | MDA concentration (pmol/mL) | % pollution | % protection |
|---|---|---|---|
| Skin (T) | 503.46 | 0.00 | / |
| Skin + α tocophérol (R) | 392.28 | 0.00 | / |
| Skin + excipient (E) | 527.60 | 0.00 | / |
| Skin + Pol-5 (P) | 498.53 | 0.00 | / |
| Skin + contaminant (TP) | 675.34 | 100.00 | 0.0 |
| Skin + α tocophérol + contaminant (RP) | 544.93 | 24.13 | 75.9 |
| Skin + excipient + contaminant (EP) | 640.40 | 79.67 | 20.3 |
| Skin + Pol-5 + contaminant (PP) | 624.06 | 55.90 | 44.1 |

The αTocophérol control has reduced pollutants activity validating the assay. Results for Pol-5 indicated potential antipollution activity.

Example 9

Effect of EPSS on Restructuration of Skin Barrier on Human Skin Explants

This assay sought to demonstrate the restructuring effect on skin barrier of tested EPSs. Biological activity was assessed by the histological expertise of general morphology, and by immunolabelling of filaggrin and membrane transglutaminase. Higher filaggrin and/or transglutaminase expression levels (e.g., in more cellular layers) are signs of increased keratinocytes differentiation.

Human skin explants were obtained from an abdominal plastic surgery of a 48-year-old woman. A zone was defatted (delipidated) using a mixture of ether/acetone to increase sensitivity to the tested EPS and to remove outside factors potentially biasing comparative results (e.g., fat thickness and content may vary along the sample and introduce parameters biasing the results between controls and test EPSS). On this delipidated zone, 24 experimental explants were obtained. Six (6) experimental explants were generated from the non-defatted section. All 30 explants were put in BEM medium and stored in an incubator at 37° C. and 5% of $CO_2$. This material was divided into 10 lots of 3 explants.

Tested EPSs were applied topically right after lipid removal at a concentration of 4 mg per explant. Contact period was 3 hours. At time T0 and 3 h, each of the 3 explants of the lot was cut into two parts. The first part was fixed in regular Bouin medium for observation of general morphology. The second half was frozen and kept in −80° C. for the specific immunolabelling of filaggrin and membrane transglutaminase.

After 48 hours of fixing in regular Bouin medium, samples were desiccated and impregnated in paraffin. Frozen samples were sliced into 7 μm thick slices in a cryostat, and then glued onto histological slides for labelling.

Observation of general morphology was accomplished using Masson type Trichrome stains. Filaggrin was marked on frozen slides at time T0 and T3 h with the anti-filaggrin, monoclonal clone OKTB1, with a biotin/streptavidin system revealed in FITC with nucleus coloured using propidium iodide staining. Transglutaminase from the membrane was marked on frozen slides at time T0 and T3 h with the anti-transglutaminase, monoclonal clone BC1, with a system biotin/streptavidin revealed in FITC with nucleus coloured using propidium iodide staining.

Filaggrin

At T0, filaggrin was slightly expressed at the base of the stratum corneum with a normal number of cellular layers in non-delipidated explants. Filaggrin was slightly more present in delipidated explants.

Figure 2:
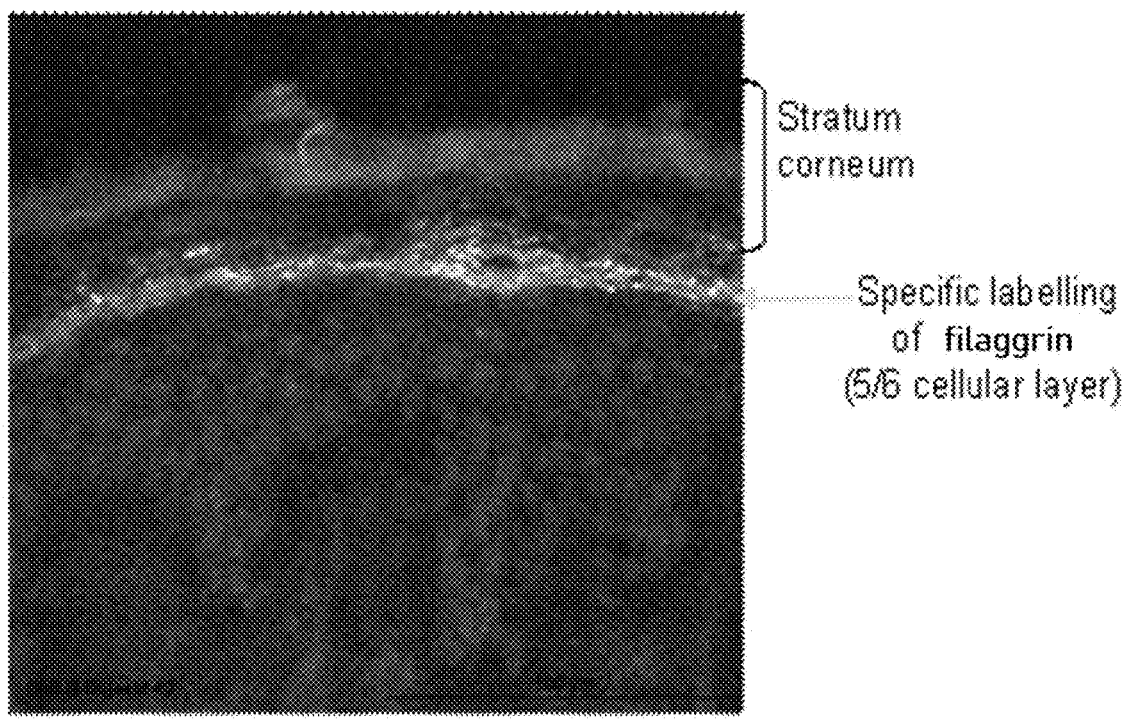
FIG. 2 shows filaggrin labelling in a non-delipidated explants after 3 hours without treatment.
Figure 3:
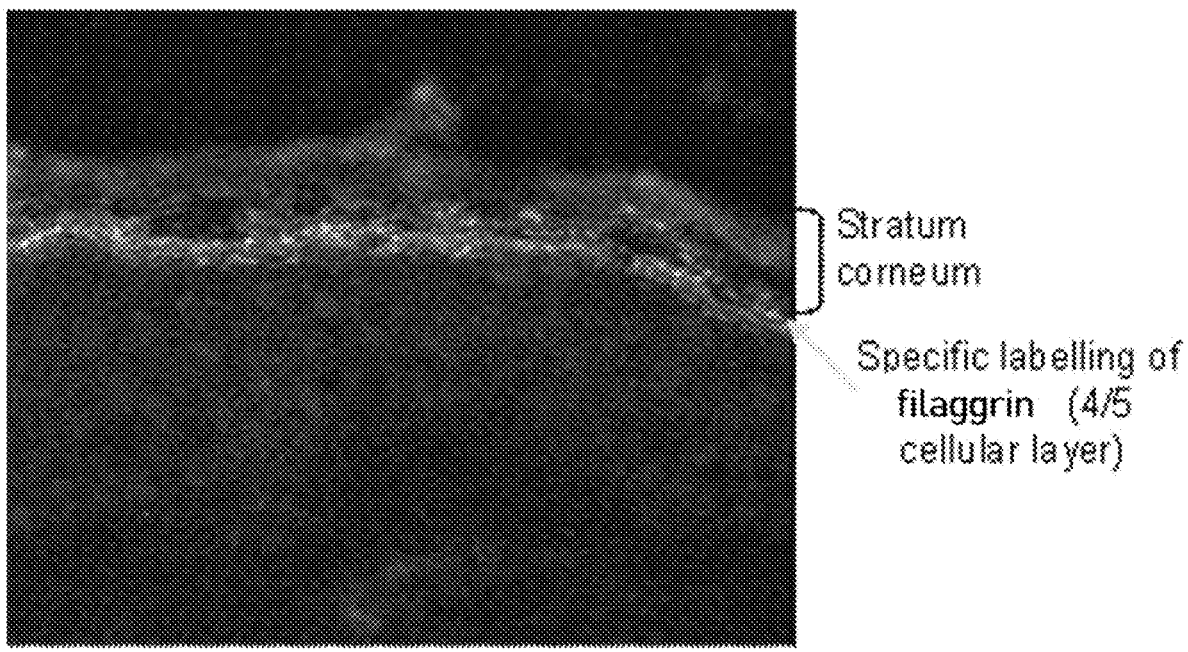
FIG. 3 shows filaggrin labelling in a delipidated explant after 3 hours without treatment.

As may be observed in FIG. 2, at 3 h, filaggrin was distinctly expressed in non-treated and non-delipidated explants. As may be observed in FIG. 3, filaggrin was slightly expressed in delipidated and non-treated explants. A moderate number of cellular layers could be observed.

Figure 4:
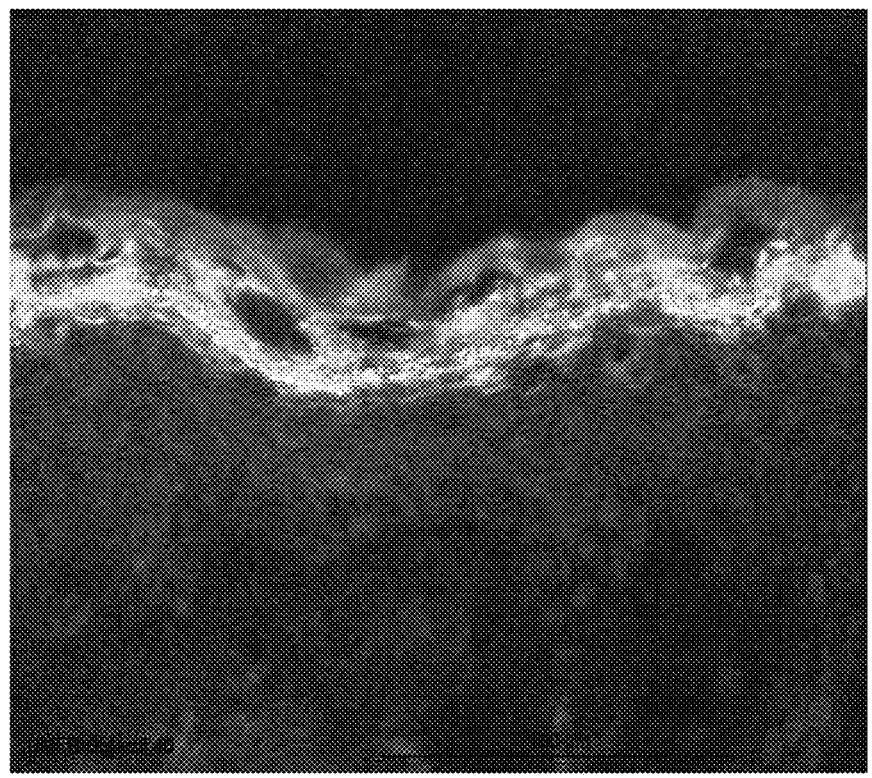
FIG. 4 shows filaggrin labelling in a delipidated explant after 3 hours with EPS treatment (Pol-6)

After application of Pol-6 (FIG. 4), Pol-3 and Pol-8 on delipidated explants, filaggrin was strongly expressed on 11/12 (Pol-6) and 8/9 cellular layers (pol-3 and 8), respectively.

Figure 5:
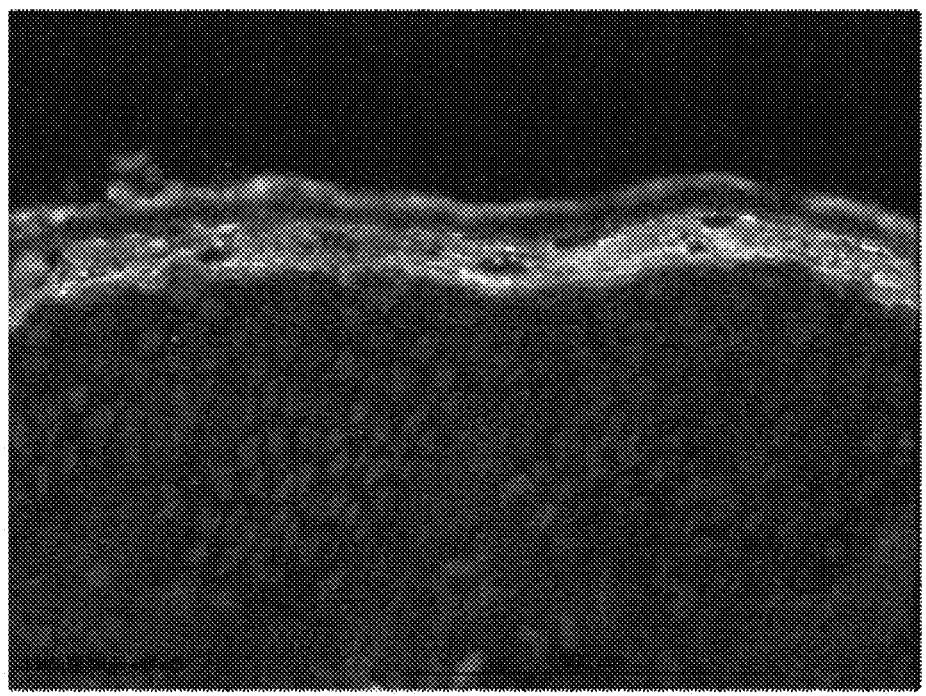
FIG. 5 shows filaggrin labelling in a delipidated explant after 3 hours with EPS treatment (Pol-6 and Pol-3)

After application of a mixture of Pol-6 and Pol-3 on delipidated explants, filaggrin was distinctly expressed on 8/9 cellular layers (FIG. 5).

Figure 6:
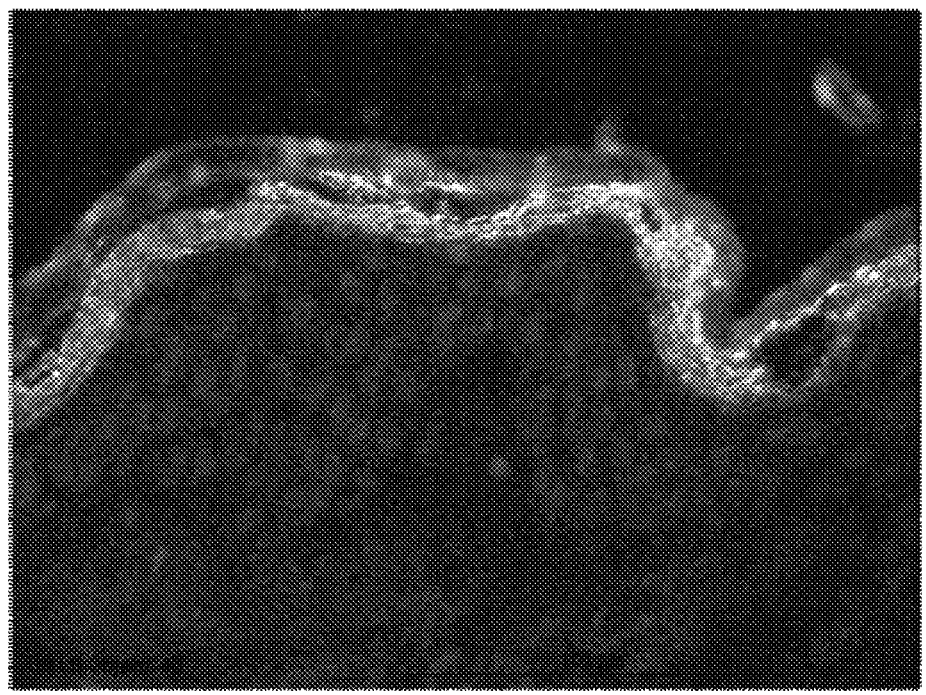
FIG. 6 shows filaggrin labelling in a delipidated explant after 3 hours with EPS treatment (Pol-6 and Pol-8)

After application of a mixture of Pol-6 and Pol-8 on delipidated explants, filaggrin is distinctly expressed on 8/9 cellular layers (FIG. 6).

Membrane Transglutaminase

At T0, transglutaminase was very slightly and erratically expressed on 3/4 cellular layers at the base of the stratum corneum in non-delipidated and non-treated explants and on freshly delipidated explants.

Figure 7:
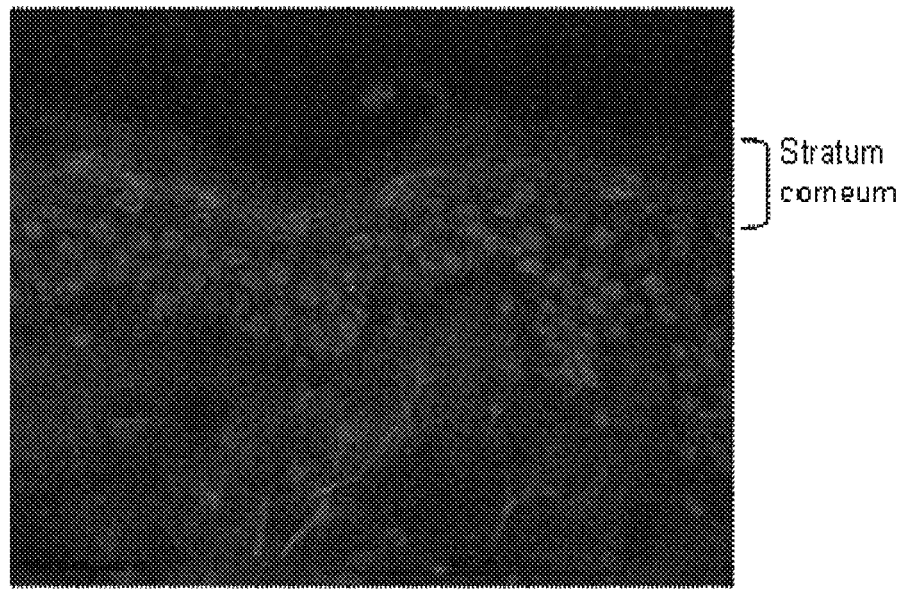
FIG. 7 shows transglutaminase labelling in a non-delipidated explant after 3 hours without treatment.
Figure 8:
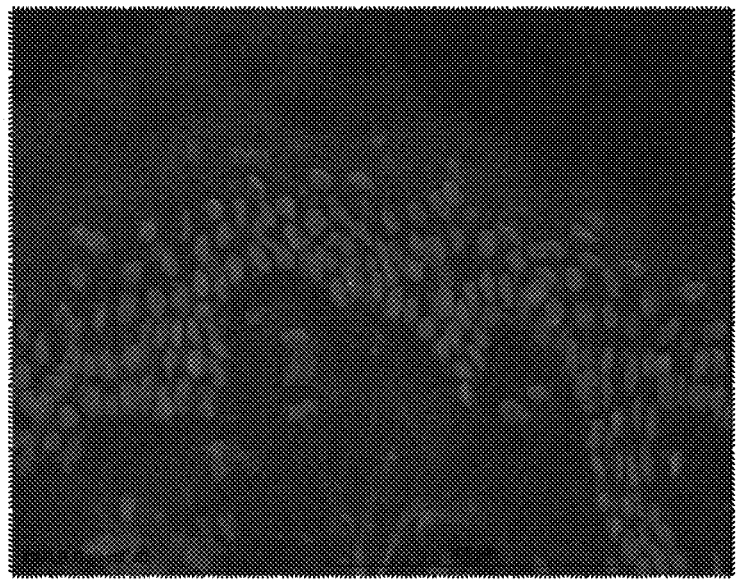
FIG. 8 shows transglutaminase labelling in a delipidated explant after 3 hours without treatment.

At 3 h, transglutaminase was very slightly expressed in non-delipidated and non-treated explants (FIG. 7). Transglutaminase was not observed on delipidated and non-treated explants (FIG. 8).

Figure 9:
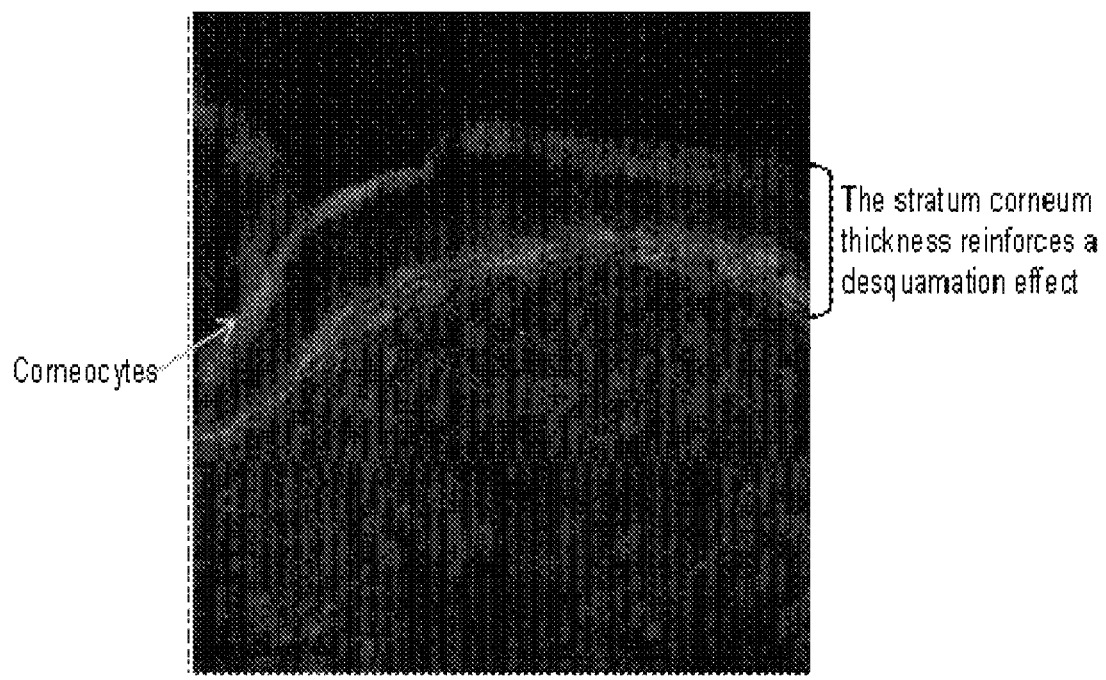
FIG. 9 shows transglutaminase labelling in a delipidated explant after 3 hours with EPS treatment (Pol-6)

For treatment with Pol-6 (FIG. 9) and Pol-3 on delipidated explants, transglutaminase was distinctly expressed on 5/6 cellular layers.

Immunostaining results of filaggrin and membrane transglutaminase (TGM) are presented in Table XIV below.

TABLE XIV

| Treatment | Filaggrin | | TGM | |
|---|---|---|---|---|
| | Intensity | Nb of cellular layer | Intensity | Nb of cellular layer |
| Non delipidated skin, T3h | +++ | 5/6 | + | 3/4 |
| Delipidated skin, T3h | ++ | 4/5 | − | − |
| Delipidated skin, treated with product Pol-6, T3h | ++++ | 11/12 | +++ | 5/6 |
| Delipidated skin, treated with product Pol-3, T3h | ++++ | 8/9 | + | 4/5 |
| Delipidated skin, treated with product Pol-8, T3h | +++ | 8/9 | − | − |
| Delipidated skin, treated with a mix of Pol-6 and 3, T3h | +++ | 8/9 | + | 2/3 |
| Delipidated skin, treated with a mix of Pol-6 and 8, T3h | +++ | 8/9 | ++ | 3/4 |

Absent: −
Low: +
Moderate: ++
Clear/Net: +++
Strong: ++++

Delipidated explants showed a very net deterioration of the stratum corneum with a comparable morphology in a dehydrated skin combined with an important impairment of the appearance of the dermis (disorder of collagen fibres).

The observation of general morphology shows that after 3 hours of contact, EPS Pol-3 improved the morphology of the stratum corneum, which would result in a superficial moisturizing activity of the stratum corneum. The mixture of Pol-3 and Pol-8 and the mixture of Pol-6 and Pol-8 improved the morphology of the stratum corneum (moisturizing effect).

EPS Pol-6 improved the structure of the skin at the level of the stratum corneum and dermis. Specifically, the general morphology showed that after 3 hours of contact with EPS Pol-6, the stratum corneum was fluffy, indicating cells renewal and desquamation. Collagen fibres appeared denser and more organized.

Filaggrin expression showed that all applied EPSs led to a net increase (intensity and number) of cellular layers after 3 hours of contact.

Membrane transglutaminase expression showed that EPS Pol-6 and the mixture Pol-6 and Pol-8 induced a restructuring activity of skin barrier.

Example 10

Clinical Testing of Hydrating and Skin Barrier Restructuring Properties of Polysaccharides-Containing Skin Care Composition The aim of this assay was to objectively assess on a panel of 20 volunteers, the moisturizing activity and the lipid barrier restructuring ability of a cream containing EPSs, after 30 days of usage. This activity was assessed compared to a placebo. Both formulations were applied using split-face design. Volunteers were recruited in the population of subjects between 30 and 50 years with skin prone to dryness. The moisturizing effect was quantitatively assessed by special marking from physiological desquamation, type D-Squames® surface sampling. Restructuring effect was assessed by analysis of the microrelief on cyanoacrylate-glued samples and by photographs.

A skin care formulation was prepared containing Pol-6 and Pol-3.

TABLE XV

| Ingredient | % W/w |
| --- | --- |
| Water | QS. for 100% w/w |
| Glyceryl Stearate | 5.00% |
| Caprylic/Capric Triglyceride | 5.00% |
| Myristyl Myristate | 3.00% |
| Butylen Glycol | 3.00% |
| Polysorbate 60 | 2.00% |
| Glycerin | 2.00% |
| Butyrospermum Parkii | 1.00% |
| Cetyl Alcohol | 1.00% |
| Phenonip | 0.80% |
| Sorbitan Stearate | 0.50% |
| Carbomer | 0.15% |
| Triethanolamine | 0.11% |
| Dimethicone | 0.04% |
| Perfume | 0.02% |
| Polysaccharide Pol-3 | .02% |
| Polysaccharide Pol-6 | .02% |
|  | 100% |

Quantitative evaluation of hydration by special marking (Diagnoskin™) using physiological desquamation.

The evaluation of cutaneous moisture level by the system DIAGNOSKIN™ was made through quantification of physiological desquamation. 18 volunteers were involved in the evaluation of the active formulation and 19 volunteers were part of the placebo group.

Figure 10:
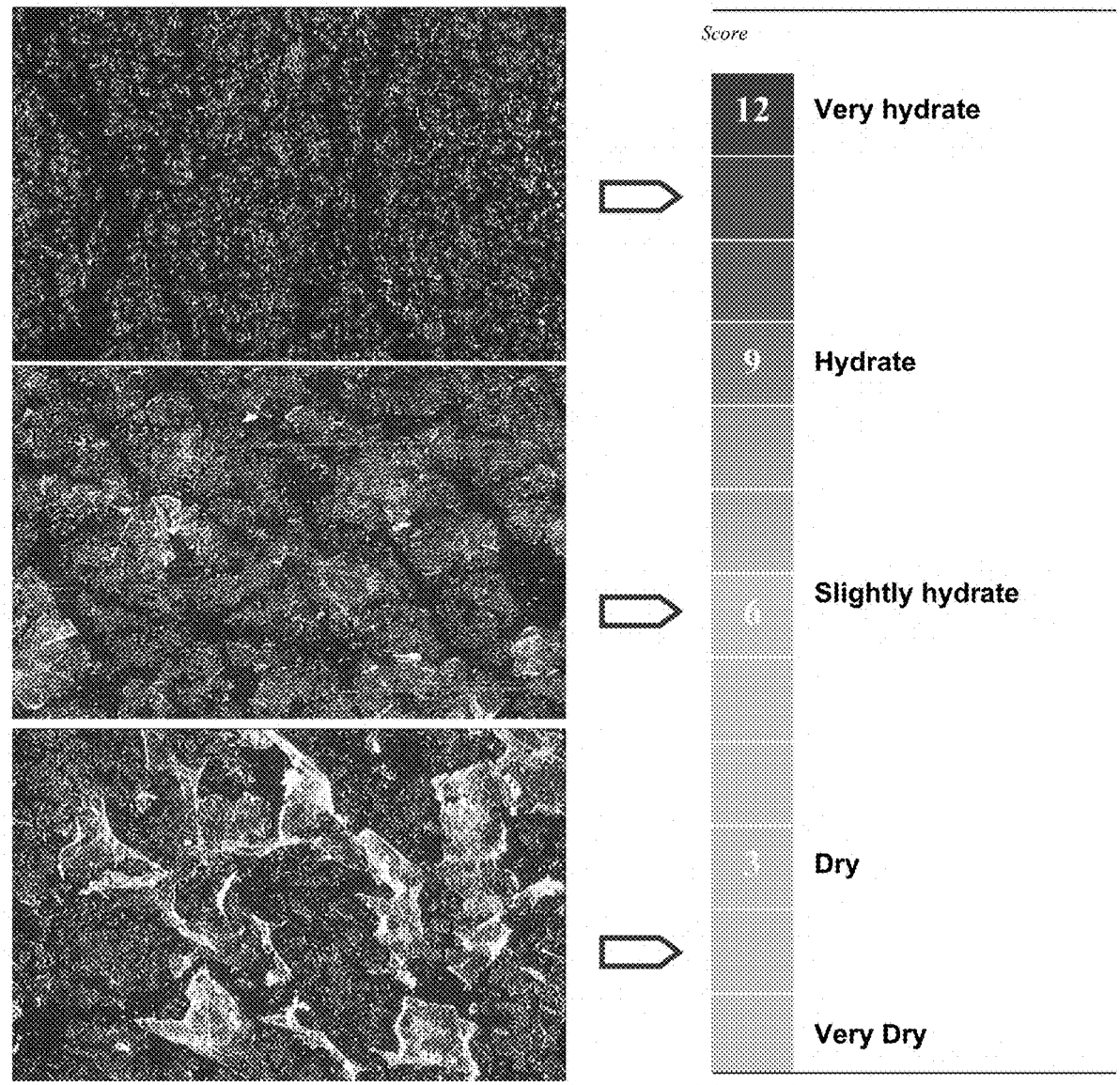
FIG. 10 shows photographs of morphology of very hydrate (upper panel) to very dry (lower panel) skin.

Application on the skin of a flexible adhesive band, D-Squam™ sampled the superficial layers of corneocytes when withdrawn. Evaluation of this desquamation was performed using a microscope (objective 25×, direct light). Based on these observations, the skin samples were rated on 1 to 12, 12 been the highest possible level of hydration. FIG. 10 shows three photographs of skin morphology from the most hydrated to the least hydrated.

Active composition: An increase of 9.82% of the quality of desquamation after 30 days of application of active cream was observed as may be seen in Table XVI below:

TABLE XVI

| | D-Squam™ scores | | |
| --- | --- | --- | --- |
| | J0 | J30 | J30-J0 |
| Average | 5.61 | 6.22 | 0.61 |
| % | | +9.82% | |

Figure 11:
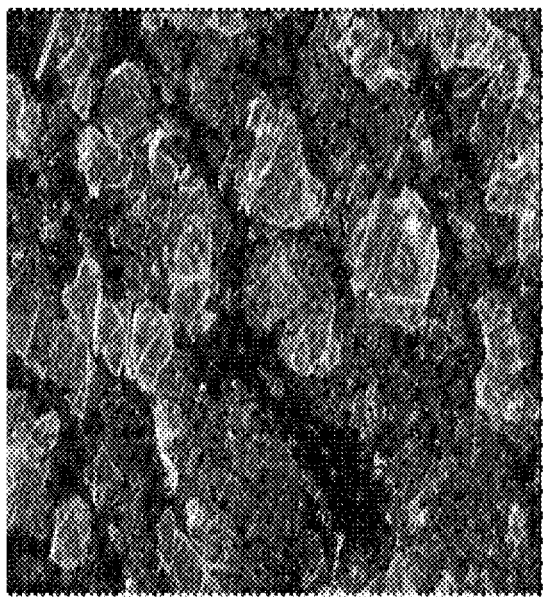
FIG. 11 shows before and after photographs of hydration state of superficial skin layers treated with EPS.
Figure 11:

The morphological aspect of the samples revealed a skin texture of a much more hydrated skin when treated with a mixture of Pol-6 and Pol-3 for 30 days. In fact, cell plates and thick zones (indicating cutaneous dehydration) noticed at T0, practically disappeared after 30 days of treatment. Single cells were then observed, synonymous of a more hydrated skin. See FIG. 11 for before and after photographs.

Placebo: a reduction of 7.14% of the quality of desquamation after 30 days of application of the placebo was observed as may be seen in the Table XVII below.

TABLE XVII

| | D-Squam™ scores | | |
| --- | --- | --- | --- |
| | J0 | J30 | J30-J0 |
| Average | 6.32 | 5.89 | −0.42 |
| % | | −7.14 % | |

Figure 12:
FIG. 12 shows before and after photographs of hydration state of superficial skin layers treated with placebo.
Figure 12:
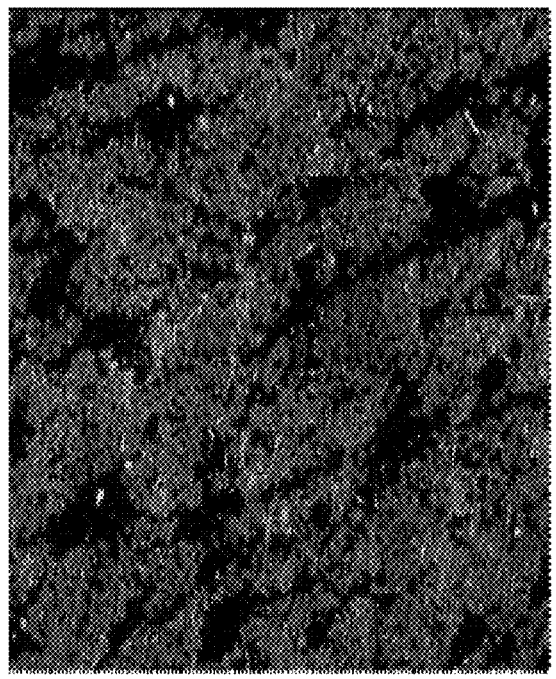

Morphological aspect of samples for volunteers having applied placebo showed an important deterioration of the skin with small cell plates indicating an increase of cutaneous dehydration. See FIG. 12 for before and after photographs.

Figure 13:
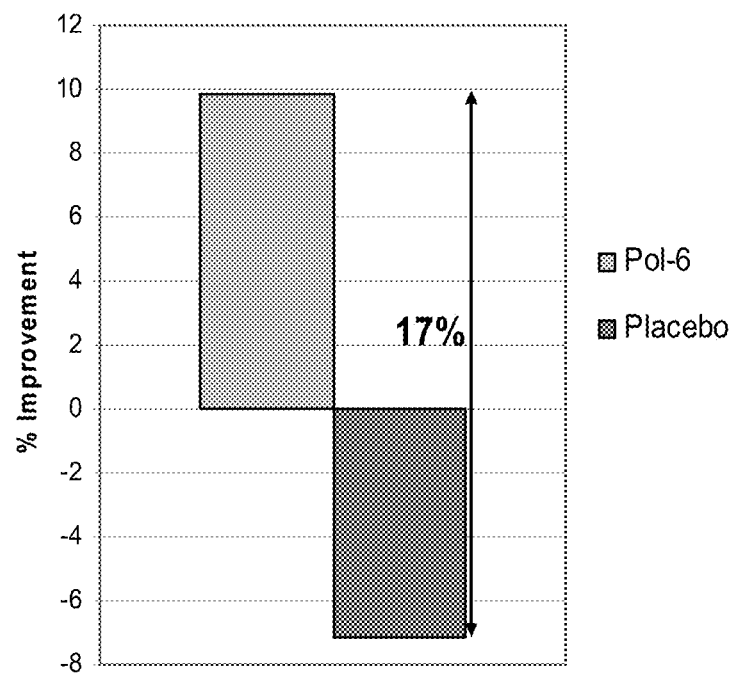
FIG. 13 graphically shows the difference in hydration between EPS and placebo treatment of FIGS. 11 and 12, respectively.

The gap between the placebo and the active cream (17%) show a clear improvement of the desquamation of the skin, linked to a higher differentiation/desquamation rate. This difference is illustrated in FIG. 13. A more efficient renewal of the superficial coats of the skin was observed in conjunction with tensing and restructuring effects responsible for a nicer and even skin.

Quantitative Evaluation of Restructuring Effect

Sampling was performed on cheekbones of 18 volunteers for active cream and placebo. Samples of surface were prepared by depositing a drop of cyanoacrylate glue directly on the skin and by applying immediately a clean histological slide. The quick polymerization (30 seconds) of the cyanoacrylate glue allows taking samples of homogeneous thickness of the external part of the stratum corneum (4-6 layers of corneocytes) without pain. Observation of the samples using a microscope (objective 2.5×) with lateral direct light allowed an evaluation taking into account the parameters of the micro-relief (primary lines, secondary lines, polygons . . . ).

Active composition: an improvement of microrelief by 9.09% was observed after 30 days of application of active cream as may be seen in Table XVIII below.

TABLE XVIII

| | Microrelief Score | | |
| --- | --- | --- | --- |
| | J0 | J30 | J30-J0 |
| Average | 4.12 | 4.53 | 0.41 |
| % | | 9.09% | |

Figure 14:
FIG. 14 shows before and after photographs of microrelief state of skin treated with EPS.
Figure 14:
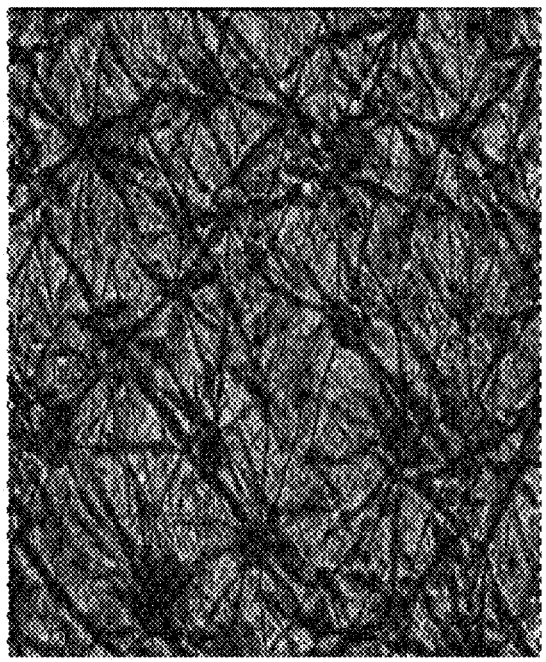

Microscopic observations of the untreated and treated skins put in contrast differences in the parameters of the microrelief. Volunteers treated during 30 days with the active cream showed a perfect organization and structure of the skin with the intersecting of primary and secondary lines forming polygons. Before treatment, these same parameters were not noticed translating the state of a dehydrated skin showing instead an orientation of primary and secondary lines along a skin tension lines (lines of tension of the skin). See FIG. 14 for before and after photographs of the skin of a treated volunteer.

Placebo composition: a reduction of 6.49% of the quality of microrelief was observed after 30 days of application of the placebo as may be seen in Table XIX below.

TABLE XIX

| | Microrelief scores | | |
| --- | --- | --- | --- |
| | J0 | J30 | J30-J0 |
| Average | 4.56 | 4.28 | −0.28 |
| % | | −6.49% | |

Figure 15:
FIG. 15 shows before and after photographs of microrelief state of skin treated with placebo.
Figure 15:

Microscopic observations of the skins of volunteers treated during 30 days with placebo shows a deterioration of microrelief with an alignment of the primary and secondary lines along skin tension lines translating a significant dehydration of the skin. See FIG. 15 for before and after photographs of the skin of a placebo-treated volunteer.

Figure 16:
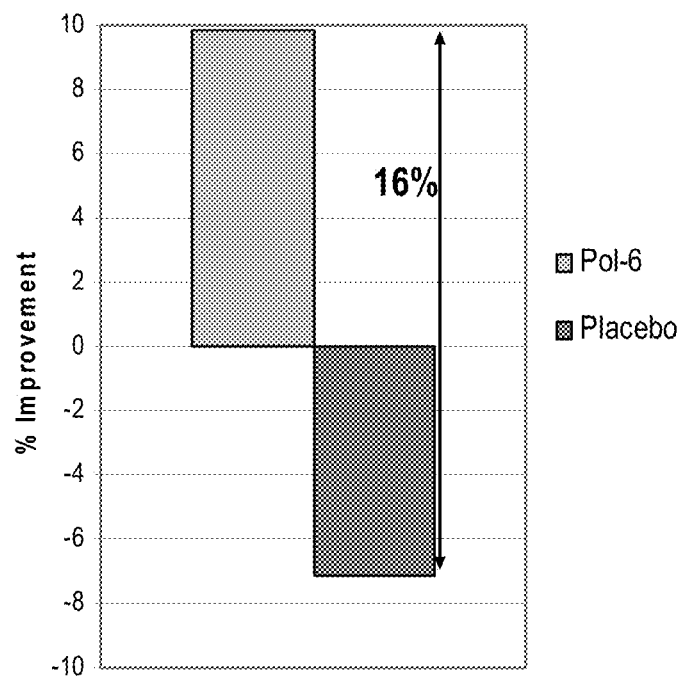
FIG. 16 graphically shows the difference in hydration between EPS and placebo treatment of FIGS. 14 and 15, respectively.

This study showed a gain of 16% in the quality of the skin microrelief with a cream formulated with exopolysaccharides. This difference is illustrated in FIG. 16.

This study evidenced the exfoliating activity of the exopolysaccharides of the invention showing improved desquamation of the skin while ameliorating its microrelief. The texture of the skin was distinctly improved.

Example 11

Clinical Testing of Anti-Pollution Properties of EPSS-Containing Skin Care Composition A clinical study was performed to determine the efficacy of the antipollution skin care with Pol-5 under normal conditions of use. For that purpose, 63 volunteers of female gender, 30 to 50 years old with a sensitive skin, living in a large city were enrolled and 50% of them were smokers. The volunteers were instructed to use the antipollution skin care described in Example 12 below twice a day during 4 weeks and to not otherwise change their cosmetic habits. They completed 2 self-administered questionnaires at D7 and D28. Data collection and material logistics were performed by mail.

Specific comments have been identified in the questionnaires of 57 respondents: respondents found the cream easy to apply, the cream had a pleasant scent, the cream had pleasant texture, the cream quickly penetrated, provided a well-being feeling, protected the skin from pollution, fought against the fatal effects due to pollution, gave a healthy look effect, left the skin more beautiful, left the complexion less dull.

After 4 weeks of standard use of a cream formulated with Pol-5, over 70% of expressed opinions are favorable. A large majority of volunteers (74.5%) rated the product as rather good (23.6%), good (34.5%) or very good (16.75). Most of remaining volunteers had a neutral opinion on the product (21.8%).

Example 12

EPSS-Containing Skin Care Formulations

Without being so limited, polysaccharides of the present invention can be included into a formulation comprising at least the following ingredients:

| Water | QS. for 100% W/W |
|---|---|
| Caprylic/ Capric Triglyceride | 5% |
| Glyceryl Stearate | 4% |
| Propylene Glycol | 3% |
| Myristyl Myristate | 3% |
| Polysorbate 60 | 2% |
| Dicaprylyl Carbonate | 2% |
| Butyrospermum Parkii | 1% |
| Stearic Acid | 1% |
| Cetyl Alcohol | 1% |
| Phenonip | 0.8% |
| Sorbitan Stearate | 0.5% |
| Carbomer | 0.15% |
| Triethanolamine | 0.15% |
| Dimethicone | 0.04% |
| Perfume | 0.01% |
| Polysaccharide Pol-5 | 0.02% |

The invention claimed is:

1. A method of reducing at least one skin aging sign in a subject comprising administering on the skin of the subject an effective amount of a composition comprising at least one isolated native exopolysaccharide (EPS), wherein the at least one EPS comprises Pol-6 and Pol-5, the at least one EPS being in a concentration of about 0.001% w/w to about 1.5% w/w of the composition, wherein:
   a) said Pol-6:
      i) has a molar ratio of about 0.7 rhamnose and 0.7 mannose for a glucose reference of 10.0, as determined by gas chromatography;
      ii) does not comprise galactose, xylose, and galacturonic acid, as determined by gas chromatography; and
      iii) is secreted by a *Vibrio alginolyticus* bacterial strain originally isolated from a kopara microbial mat; and
   b) said Pol-5:
      i) has a molar ratio of about 3.2 D-glucose, 2.9 D-galactose, 0.5 D-mannose, 2.0 D-glucuronic acid and 1.0 D-galacturonic acid, as determined by gas chromatography; and
      ii) is secreted by an *Alteromonas macleodii* bacterial strain originally isolated from a kopara microbial mat;
   wherein at least one skin aging sign is reduced.

2. The method of claim 1, wherein the method improves the morphology of stratum corneum.

3. The method of claim 1, wherein the method improves skin desquamation.

4. The method of claim 1, wherein the method improves keratinocytes differentiation.

5. The method of claim 1, wherein the method decreases bacterial adhesion on skin surface.

6. The method of claim 1, wherein the method stimulates epidermis total lipid synthesis.

7. The method of claim 1, wherein the method stimulates the expression of at least one gene involved in skin desquamation.

8. The method of claim 7, wherein the at least one gene encodes kallikrein 5, neurosin or stratum corneum chymotryptic enzyme.

9. The method of claim 1, wherein the method stimulates the expression of at least one gene involved in keratinocytes differentiation.

10. The method of claim 9, wherein the at least one gene encodes filaggrin, loricrin or involucrin.

11. The method of claim 1, wherein the method stimulates the expression of transglutaminase.

12. The method of claim 1, wherein each EPS originates from a different kopara microbial mat.

13. A method of reducing at least one skin aging sign in a subject, comprising administering an effective amount of at least one isolated native exopolysaccharide (EPS) on the skin of the subject, wherein the at least one EPS comprises Pol-6 and Pol-5, and wherein:
   a) said Pol-6:
      i) has a molar ratio of about 0.7 rhamnose and 0.7 mannose for a glucose reference of 10.0, as determined by gas chromatography;

ii) does not comprise galactose, xylose, and galacturonic acid, as determined by gas chromatography; and iii) is secreted by a *Vibrio alginolyticus* bacterial strain originally isolated from a kopara microbial mat; and b) said Pol-5:

i) has a molar ratio of about 3.2 D-glucose, 2.9 D-galactose; 0.5 D-mannose, 2.0 D-glucuronic acid and 1.0 D-galacturonic acid, as determined by gas chromatography; and ii) is secreted by an *Alteromonas macleodii* bacterial strain originally isolated from a kopara microbial mat;

wherein at least one skin aging sign is reduced.

14. The method of claim 13, wherein each EPS originates from a different kopara microbial mat.

* * * * *